US012765929B2

(12) United States Patent
Bisaccia

(10) Patent No.: US 12,765,929 B2
(45) Date of Patent: Oct. 20, 2026

(54) INTERLOCK FASTENER

(71) Applicant: Xander Medical, Williston, VT (US)

(72) Inventor: Alexandra Bisaccia, Williston, VT (US)

(73) Assignee: Xander Medical, Williston, VT (US)

(*) Notice: Subject to any disclaimer, the term of this patent is extended or adjusted under 35 U.S.C. 154(b) by 0 days.

(21) Appl. No.: 19/059,668

(22) Filed: Feb. 21, 2025

(65) Prior Publication Data

US 2025/0268637 A1 Aug. 28, 2025

Related U.S. Application Data

(60) Provisional application No. 63/557,170, filed on Feb. 23, 2024.

(51) Int. Cl.
*A61B 17/86* (2006.01)
*A61B 17/88* (2006.01)
*A61B 17/56* (2006.01)

(52) U.S. Cl.
CPC ...... *A61B 17/8615* (2013.01); *A61B 17/8625* (2013.01); *A61B 17/864* (2013.01); *A61B 17/888* (2013.01); *A61B 17/8888* (2013.01); *A61B 2017/564* (2013.01)

(58) Field of Classification Search
CPC .................................................. A61B 17/8615
See application file for complete search history.

(56) References Cited

U.S. PATENT DOCUMENTS

| | | | | |
|---|---|---|---|---|
| 2003/0187447 | A1 | 10/2003 | Ferrante | |
| 2009/0287218 | A1 | 11/2009 | Beger | |
| 2012/0226318 | A1 | 9/2012 | Wenger | |
| 2013/0125714 | A1 | 5/2013 | Dahners | |
| 2020/0375750 | A1* | 12/2020 | Abbasi .............. | A61B 17/8605 |

FOREIGN PATENT DOCUMENTS

| | | |
|---|---|---|
| WO | 2023069347 | 4/2023 |

* cited by examiner

*Primary Examiner* — Olivia C Chang
(74) *Attorney, Agent, or Firm* — Van Pelt, Yi & James LLP

(57) ABSTRACT

A fastener device has a proximal head, a shaft extending from the proximal head and having external threads on at least a portion of the shaft, and a chamber extending internally from the proximal head into the shaft. At least a portion of the chamber has internal threads. The external threads have a first handedness, and the internal threads have a second handedness different from the first handedness.

18 Claims, 26 Drawing Sheets

INSERTION

1 SETUP

Insert the *INTERLOCK DRIVER* into the *INTERLOCK SCREW*'s left-handed internally threaded chamber by rotating counter-clockwise (CCW)

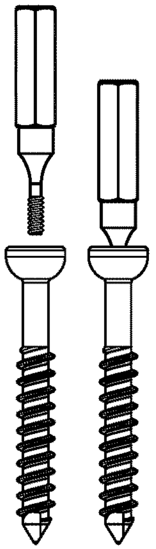

2 INSERTION

Place at desired position and insert the screw by rotating clockwise (CW) into the bone until the opposing torque value unscrews the *INTERLOCK DRIVER* from the internal threads

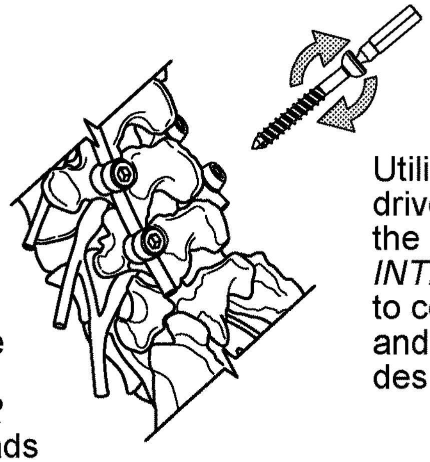

3 TIGHTEN

Utilize a secondary driver to interface with the head of the *INTERLOCK SCREW* to complete insertion and fasten to the desired tightness

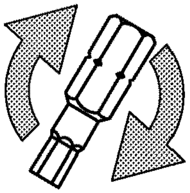

FIG. 11B

INTERLOCK FASTENER

CROSS REFERENCE TO OTHER APPLICATIONS

This application claims priority to U.S. Provisional Patent Application No. 63/557,170 entitled INTERLOCK SCREW filed Feb. 23, 2024, which is incorporated herein by reference for all purposes.

BACKGROUND OF THE INVENTION

Surgical screws are the most implanted medical device in the world, with billions of units being implanted in the global population every year. Many of those screws will be removed within 24 months of entering the body. A survey of national inpatient data samples found that 10% of spinal, hip, pelvis, and femur fixations will be removed or revised within 12 months of implantation, with rates increasing up to 80% over subsequent years in certain cases. Surgical screws are frequently damaged during insertion, patient recovery, or while attempting to be removed. With current surgical screws, it is reported that on average, 48% of surgical screws are stripped during insertion with some surgeons stripping up to 90% of the screws they implant. Additionally, many more are stripped during removal or revision surgeries. Removing stripped or otherwise damaged screws during or post-surgery can be a challenging task for surgeons; current methods of damaged screw removal can contribute to the risk of additional complications including, but not limited to, infection, secondary fractures, and metal debris in the operating field. For revision surgeries, current methods of screw removal may require relocation of the entire fixation device, further increasing procedural time and rates of other complications. Additionally, due to nonmagnetic requirements for MRI compatibility, screws are often unreliably secured to a driver via press fit or other insecure techniques. This can result in the fumbling of screws during installation and result in the risk of dropping a screw in an operating room or into the open operating field of a patient, leading to further complications and extended procedural duration.

BRIEF DESCRIPTION OF THE DRA WINGS

Various embodiments of the invention are disclosed in the following detailed description and the accompanying drawings.

FIG. 11B is a diagram illustrating an example implementation of at least a portion of the process of FIG. 11A.

DETAILED DESCRIPTION

Figure 1A:
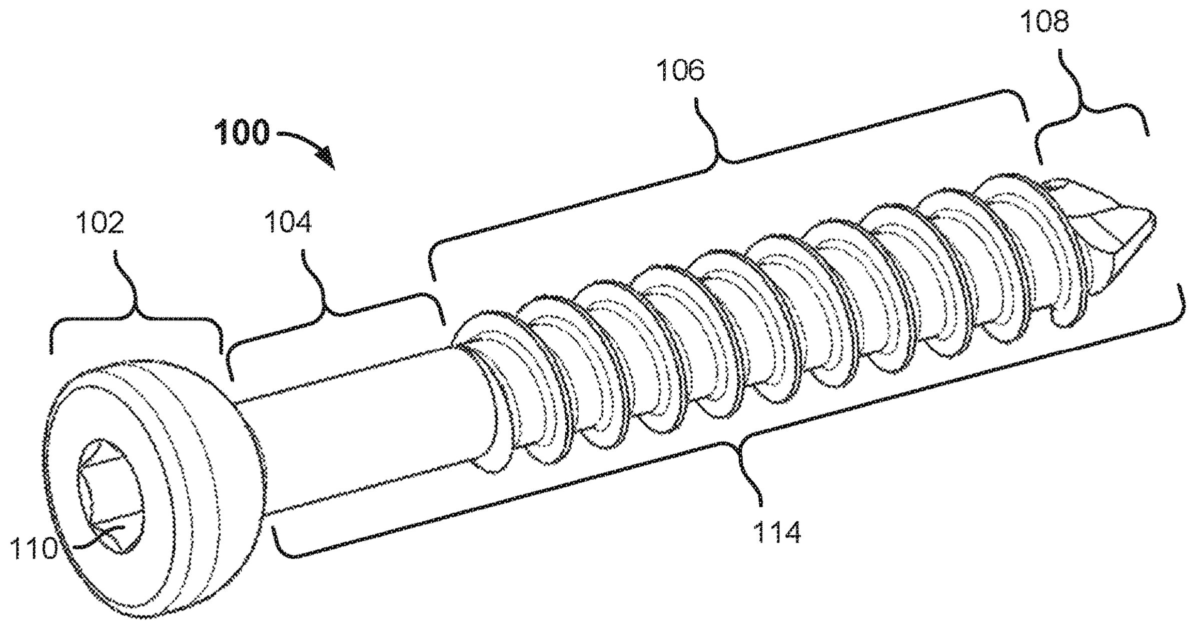
FIGS. 1A-1C are diagrams illustrating various views of an embodiment of a fastener.

The invention can be implemented in numerous ways, including as a process; an apparatus; a system; and/or a composition of matter; a computer program product embodied on a computer readable storage medium; and/or a processor, such as a processor configured to execute instructions stored on and/or provided by a memory coupled to the processor. In this specification, these implementations, or any other form that the invention may take, may be referred to as techniques. In general, the order of the steps of disclosed processes may be altered within the scope of the invention. Unless stated otherwise, a component such as a processor or a memory described as being configured to perform a task may be implemented as a general component that is temporarily configured to perform the task at a given time or a specific component that is manufactured to perform the task. As used herein, the term 'processor' refers to one or more devices, circuits, and/or processing cores configured to process data, such as computer program instructions.

A detailed description of one or more embodiments of the invention is provided below along with accompanying figures that illustrate the principles of the invention. The invention is described in connection with such embodiments, but the invention is not limited to any embodiment. The scope of the invention is limited only by the claims and the invention encompasses numerous alternatives, modifications and equivalents. Numerous specific details are set forth in the following description in order to provide a thorough understanding of the invention. These details are provided for the purpose of example and the invention may be practiced according to the claims without some or all of these specific details. For the purpose of clarity, technical material that is known in the technical fields related to the invention has not been described in detail so that the invention is not unnecessarily obscured.

Embodiments described herein allow for a screw to easily be removed if it is stripped, broken, or otherwise damaged. This can save the patient's precious biomaterial by avoiding the need to remove the material surrounding the damaged screw in order to free it, and/or prevent the need to utilize extractor kits, or extensive procedures. Additionally, embodiments described herein allow more precise insertion techniques while reducing the risk of dropping or fumbling pieces of hardware in the operating room during a surgical procedure. Alongside external threads, the screw includes an internally threaded chamber that allows the screw to be removed without relying only on the screw head. In some embodiments, the external threads are right-handed, while the internal threads are left handed. The right-handed external threads and left-handed internal threads hold a dual purpose for both removal and insertion.

In some embodiments, a fastener device (e.g., a screw) includes a proximal head, a shaft extending from the proximal head and having external threads on at least a portion of the shaft, and a chamber extending internally from the proximal head into the shaft, at least a portion of the chamber having internal threads. The external threads have a first handedness and the internal threads have a second handedness different from the first handedness. For example, by having different handedness, it allows a tool engaged with the internal threads to remain engaged with the fastener when being turned in the direction to tighten the tool within the fastener's internal chamber while the external threads of the fastener being turned in the same direction are being loosened (backed out) from a patient during orthopedic and other surgical procedures. Additionally, when screwing in the fastener to a patient, the internal threads can be used to retain the fastener on to the tool in a more secure manner as compared to traditional press fit or tacking techniques. Other embodiments do not need to achieve all these objectives, and the claims hereof should not be limited to structures or methods capable of achieving these objectives.

In an example screw insertion, an interlock driver tool (e.g., driver bit) is secured into the left-handed internal threads of the screw by rotating counterclockwise. Once the driver tool is fully seated and preloaded to a set number, the provider will rotate the screw clockwise, interfacing the external right-handed threads with the bone. The opposing torque created by the external threads when being seated into the bone will unscrew the interlock driver tool from the internal left-handed threads and the tool will be removed from the screw. Once the interlock driver tool is removed from the screw, a secondary driver tool is utilized to interface with the head of the screw and rotated in the clockwise direction to complete the insertion and fasten the screw to a desired tightness. In an example screw removal, an interlock driver tool (e.g., driver bit) is secured into the left-handed internal threads of the screw by rotating counterclockwise. Once the driver tool is fully seated, the continued counterclockwise rotation will unscrew the screw's external right-handed threads and allow for the complete removal of the screw.

In some embodiments, features of the opposing handedness thread designs of the internal threads and the external threads are governed by a relative torque relationship. The torque relationship provides a calculated approach to how the internal and external threads relate to each other when subjected to insertion and removal torque values. To achieve desired torque values at a given load, the thread pitch and thread profile dimensions are selected so that the mechanical advantage and frictional conditions produce the desired torque relationship.

Figure 1B:
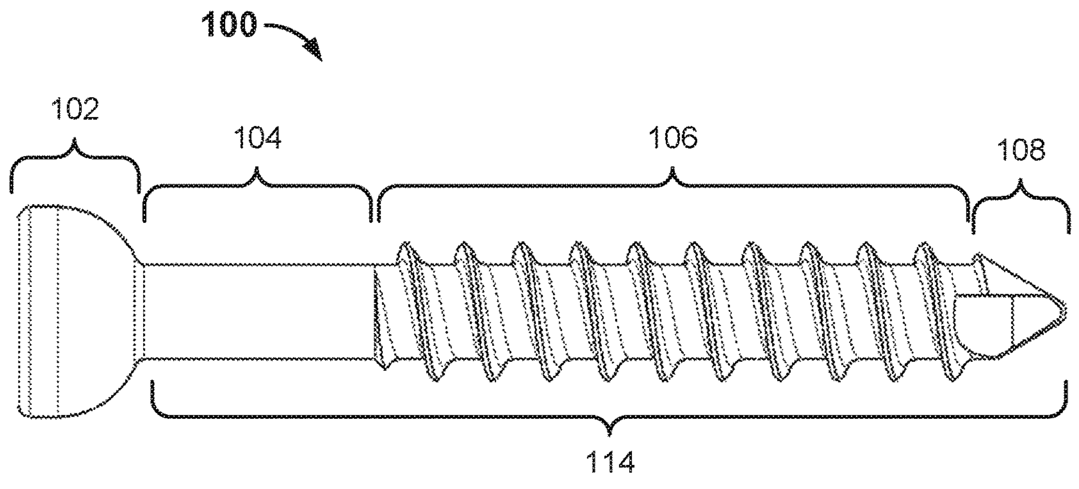
Figure 1C:
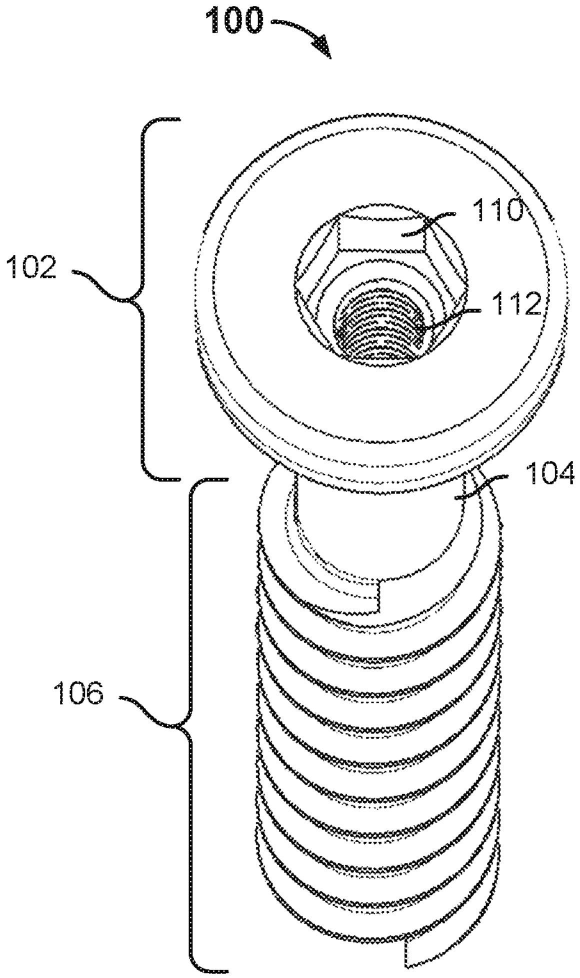
Figure 1D:
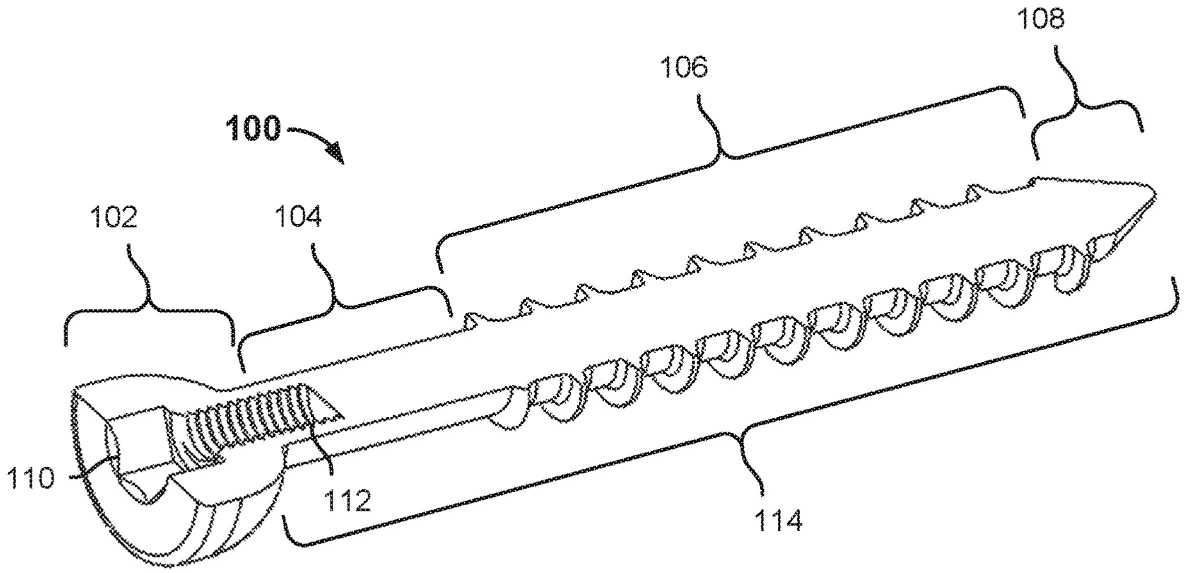
FIGS. 1D-1E are diagrams illustrating section views of an embodiment of the fastener.
Figure 1E:
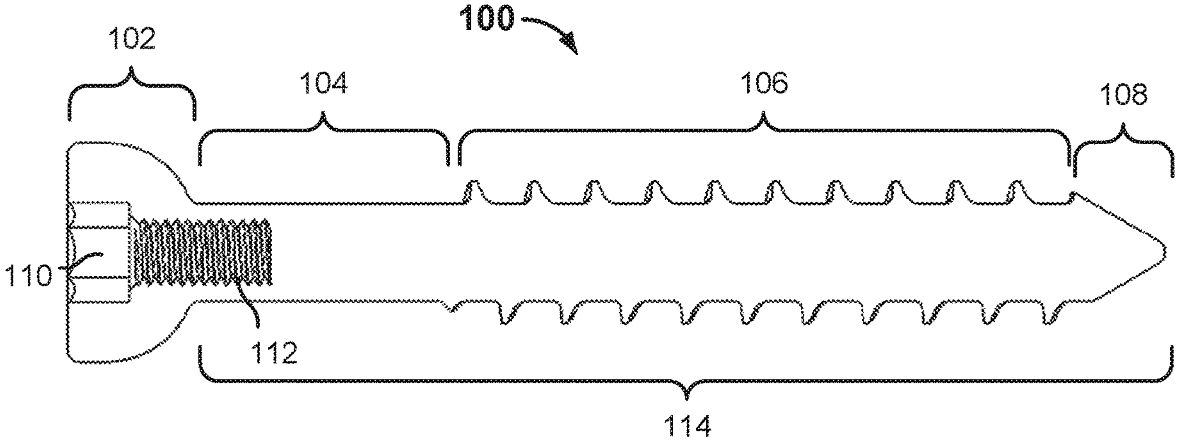
Figure 1F:
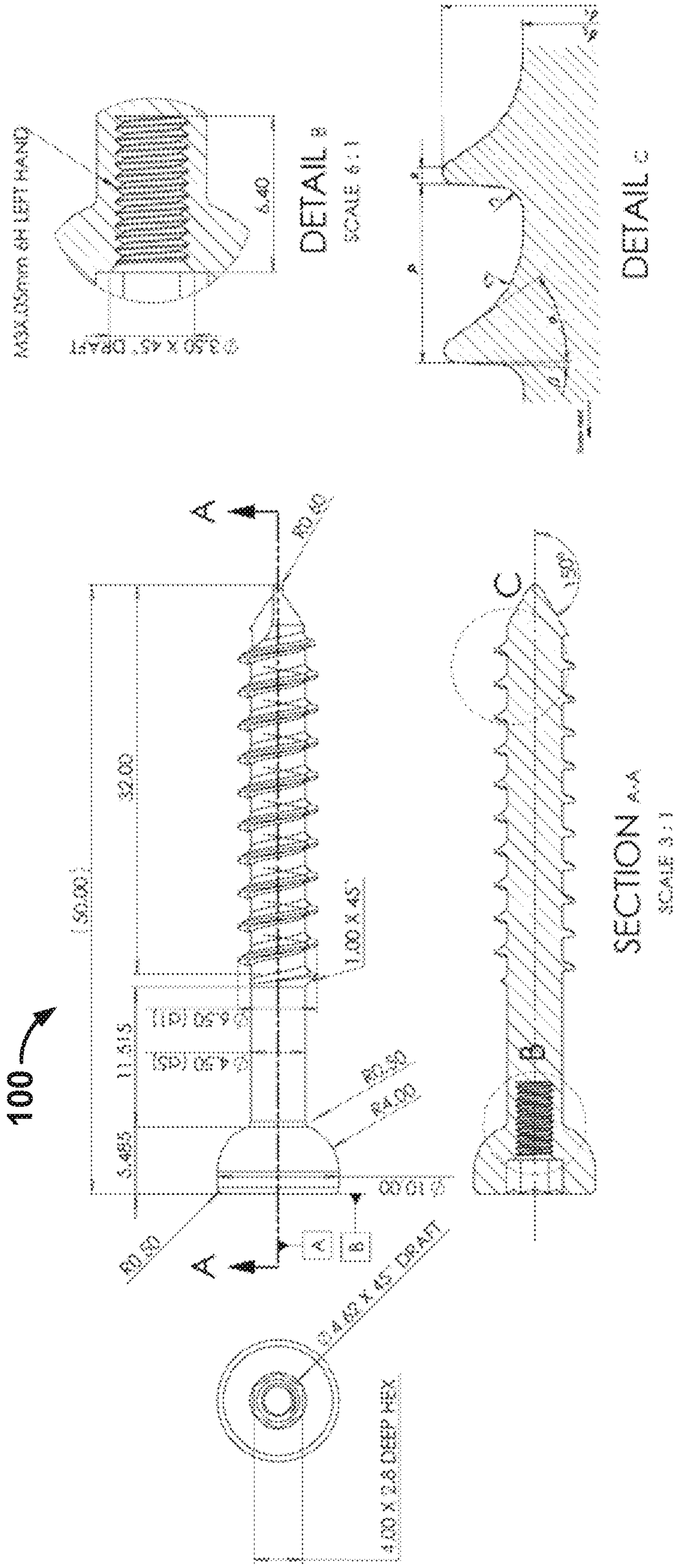
FIG. 1F is a diagram illustrating example dimensions of an embodiment of the fastener.

FIGS. 1A-1C are diagrams illustrating various views of an embodiment of a fastener. FIGS. 1D-1E are diagrams illustrating section views of an embodiment of the fastener. FIG. 1F is a diagram illustrating example dimensions of an embodiment of the fastener. Fastener 100 (e.g., screw) includes head 102, shank 104, external threads 106, tip 108, drive recess 110, internal threads 112, and shaft 114. In some embodiments, fastener 100 is made of titanium, tin, brass, bronze, copper, aluminum, nickel, zinc, iridium, or another non-ferrous metal. In some embodiments, fastener 100 is made of a biocompatible polymer or plastic. In some embodiments, fastener 100 is made of stainless steel, steel, or another ferrous metal. In various embodiments, head 102 may be one of the following types: flat, round, locking, headless, low profile, or pedicle. In an alternative embodiment, head 102 is shaped as an external drive, allowing a socket tool or an external gripping tool to engage head 102 to turn fastener 100. Examples of external drive head forms include hex, square, pentagon, star/torx or 12 point. Shank 104 is a smooth unthreaded portion between head 102 and portion of external threads 106 that may improve shear strength and prevent over-tightening of fastener 100. Shank 104 is optional in various other embodiments (e.g., entire body of fastener is threaded). In some embodiments, handedness of external threads 106 is right-handed (e.g., threads spiral in a clockwise direction so that the fastener is tightened by turning the fastener clockwise). In some embodiments, handedness of external threads 106 is left-handed (e.g., threads spiral in a counterclockwise direction so that the fastener is tightened by turning the fastener counterclockwise). Although shape/threads of a cancellous screw are shown in external threads 106, other types of threads may be utilized in other embodiments (e.g., cortical, lag, compression, fenestrated, etc.). Tip 108 may be self-tapping, self-drilling, or non-self-tapping in various embodiments. In some embodiments, shaft 114 includes a hollow center tunnel that spans the entire length of the fastener (e.g., cannulated screws).

Drive recess 110 includes an internal recess on a top of fastener 100 shaped/configured to engage a drive tool to rotate fastener 100. Although an internal hex drive type is shown in drive recess 110, drive types/shapes in other embodiments include slotted, cruciform, square, pentalobular, hexalobular (e.g., star/torx), triangular, or tamper-resistant. Drive recess 110 forms an opening part of a cavity with internal threads 112. Handedness of internal threads 112 on walls of the cylindrical cavity is opposite the handedness of external threads 106. In some embodiments, when handedness of external threads 106 is right-handed, the handedness of internal threads 112 is left-handed (e.g., threads spiral in a counterclockwise direction so that a tool engaged with the internal threads is loosened by turning the tool clockwise and tightened by turning the tool counterclockwise). In some embodiments, when handedness of external threads 106 is left-handed, the handedness of internal threads 112 is right-handed (e.g., threads spiral in a clockwise direction so that a tool engaged with the internal threads is tightened by turning the tool counterclockwise and tightened by turning the tool clockwise). The chamber with internal threads 112 is closed on the bottom and open on the top through drive recess 110. Because biomaterial can accumulate inside this partially enclosed cavity, after installation of the fastener in a subject, the cavity with internal threads 112 may be in part filled with hydrogel or another soluble and/or biocompatible material to reduce the accumulation of biomaterial inside the cavity. During removal of the fastener, this filler material may be scraped out or removed prior to screwing in a driver tool into the cavity with internal threads 112. In the absence of a filler material, a pick tool may be utilized during the removal of the fastener to scrape out accumulated biomaterial. In an alternative embodiment, the cavity with internal threads is also open on the bottom so that a hollow opening spans the entire length of the fastener from the head to the tip of the fastener (e.g., cannulated screw). Dimensions (e.g., millimeter dimensions and/or angles) shown in FIG. 1F are merely examples and fasteners with different dimensions exist in other embodiments. In various embodiments, the diameter of the fastener (e.g., distance between external threads) is greater or equal to 6 mm.

Figure 2A:
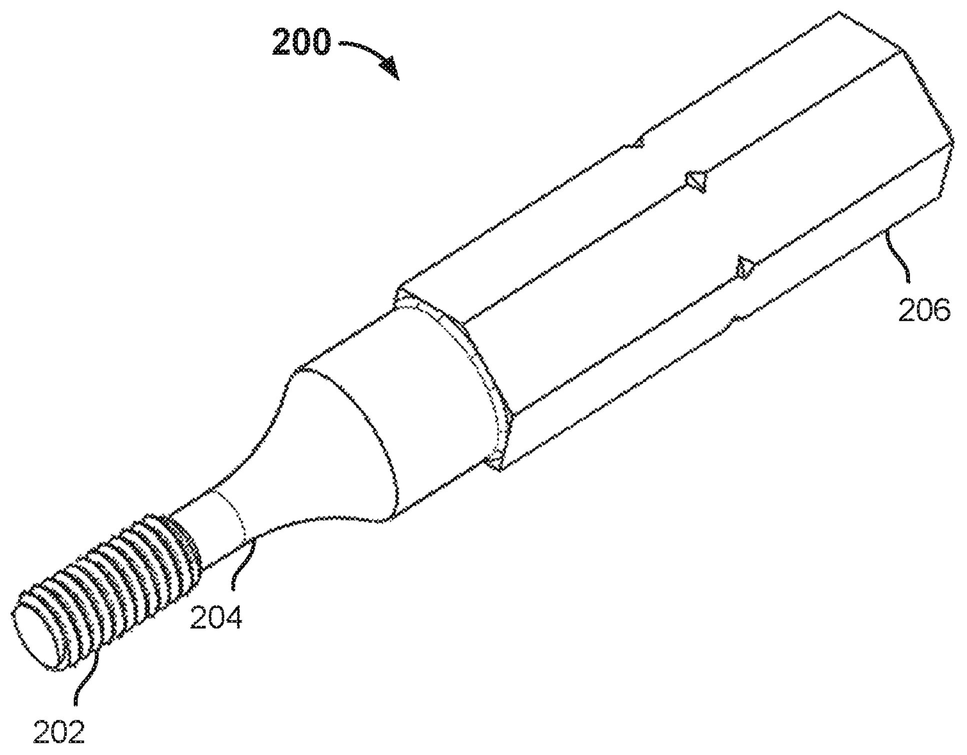
FIG. 2A is a diagram illustrating an embodiment of an interlock driver tool.
Figure 2B:
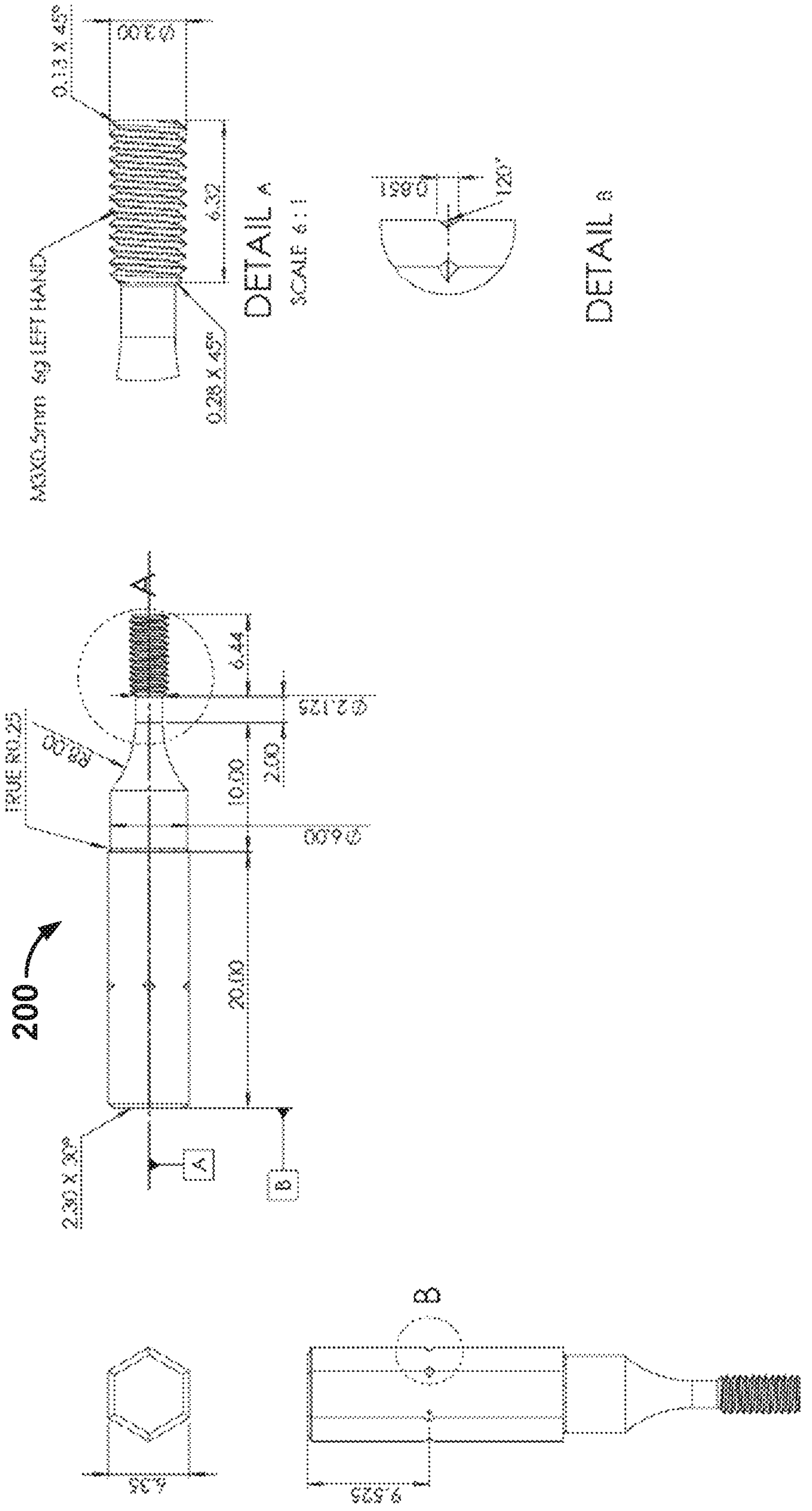
FIG. 2B is a diagram illustrating example dimensions of an interlock driver tool.

FIG. 2A is a diagram illustrating an embodiment of an interlock driver tool. FIG. 2B is a diagram illustrating example dimensions of the interlock driver tool. Interlock driver tool 200 (e.g., driver bit) includes distal tip 202 with threads, neck portion 204, and shank 206. Threads of tip 202 are configured to cooperate with internal threads 112 of fastener 100 shown in FIGS. 1A-1F. Neck portion 204 is tapered and shaped to not engage drive recess 110 of fastener 100 when tip 202 is engaged with internal threads 112. Shank 206 is configured to engage a chuck or a driver bit retainer of a driver power or hand tool. The shape/configuration of shank 206 provides a secure connection between interlock driver tool 200 and the power/hand tool (e.g., screwdriver) and transmits the rotational force from the power/hand tool to the working tip 202. Although shown shank 206 is of a hex type, other embodiments may be of a different shank type (e.g., SDS, straight, etc.) or designed as a manual screwdriver. Dimensions (e.g., millimeter dimensions and/or angles) shown in FIG. 2B are merely examples and tools with different dimensions exist in other embodiments.

Figure 3A:
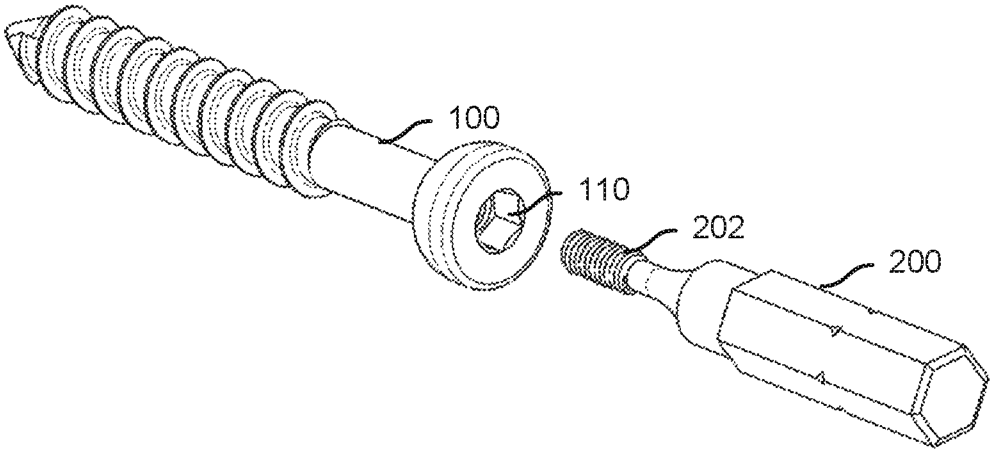
FIGS. 3A-3C are diagrams illustrating examples of engaging an interlock driver tool with a fastener.
Figure 3B:
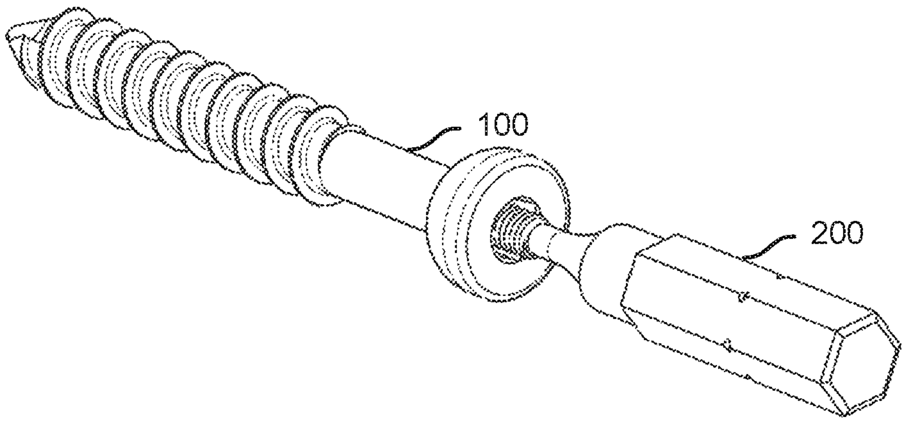
Figure 3C:
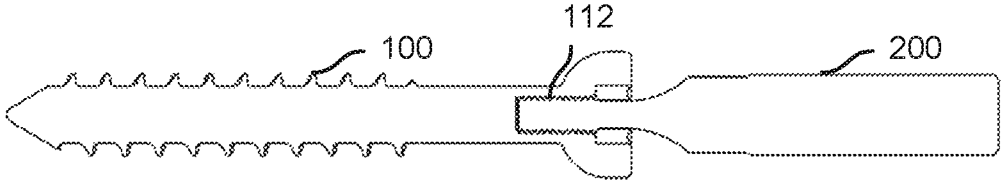

FIGS. 3A-3C are diagrams illustrating examples of engaging an interlock driver tool with a fastener. Interlock driver tool 200 of FIGS. 2A-2B is screwed into fastener 100 of FIGS. 1A-1F. Tip 202 of interlock driver tool 200 is passed through drive recess 110 and engaged with internal threads 112 of the cavity of interlock driver tool 200 by screwing tip 202 into fastener 100 until tip 202 is fully seated in the cavity having internal threads 112.

Figure 4:
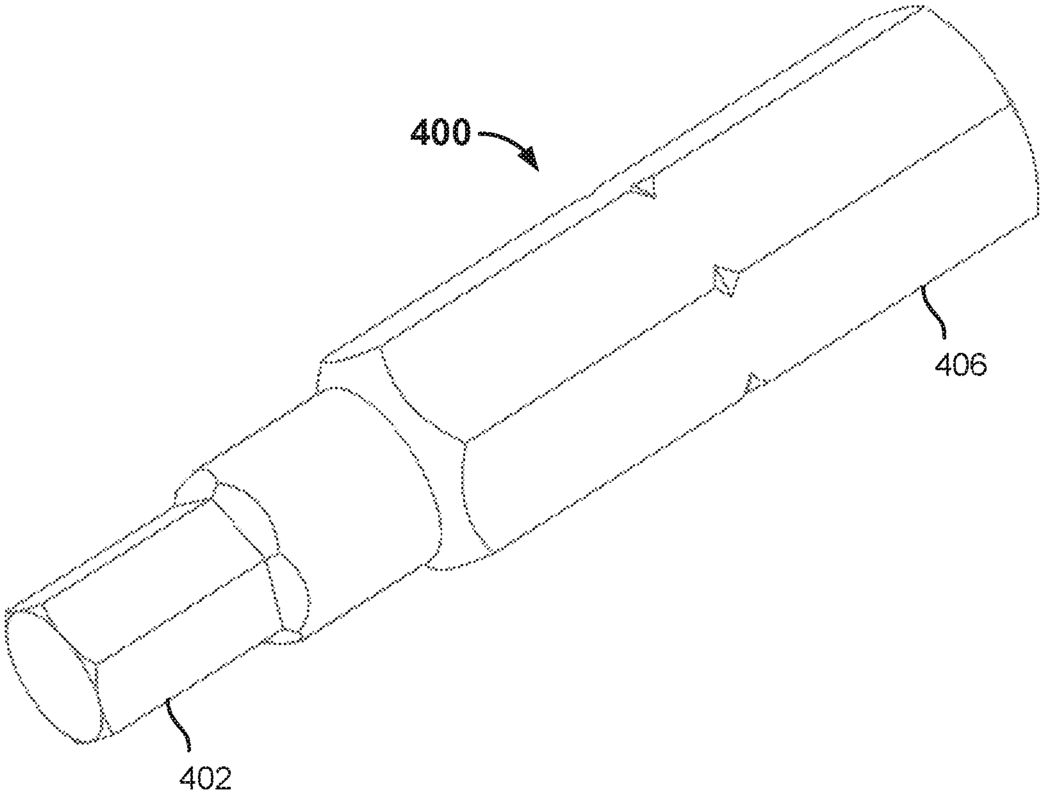
FIG. 4 is a diagram illustrating an embodiment of a head driver tool.

FIG. 4 is a diagram illustrating an embodiment of a head driver tool. Head driver tool 400 (e.g., driver bit) includes distal tip 402 and driver engagement shank 406. Hex tip 402 is configured to cooperate with internal walls of drive recess 110 of fastener 100 shown in FIGS. 1A-1F. Although tip 402 is of a hex shape/type, in other embodiments, the tip shape/type of the head driver tool in other embodiments includes slotted, cruciform, square, pentalobular, hexalobular (e.g., star/torx), triangular, or tamper-resistant. Shank 406 is configured to engage a chuck or a driver bit retainer of a driver power or hand tool. Shape/configuration of shank 406 provides a secure connection between head driver tool 400 and the power/hand tool (e.g., screwdriver) and transmits the rotational force from the power/hand tool to the working tip 402. Although as shown shank 406 is of a hex type, other embodiments may be of a different shank type (e.g., SDS, straight, etc.) or designed as a manual screwdriver.

Figure 5A:
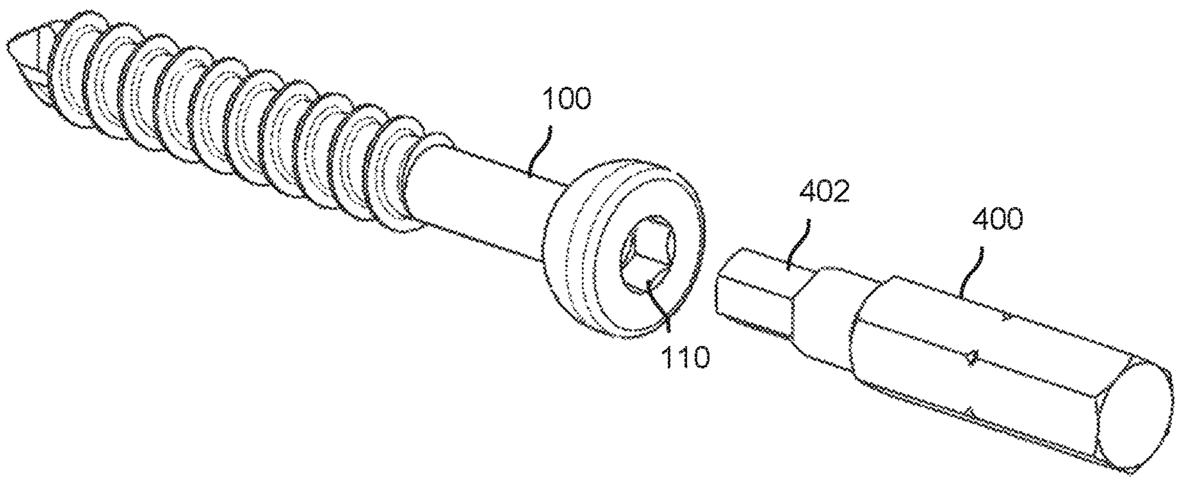
FIGS. 5A-5C are diagrams illustrating examples of engaging a head driver tool with a fastener.
Figure 5B:
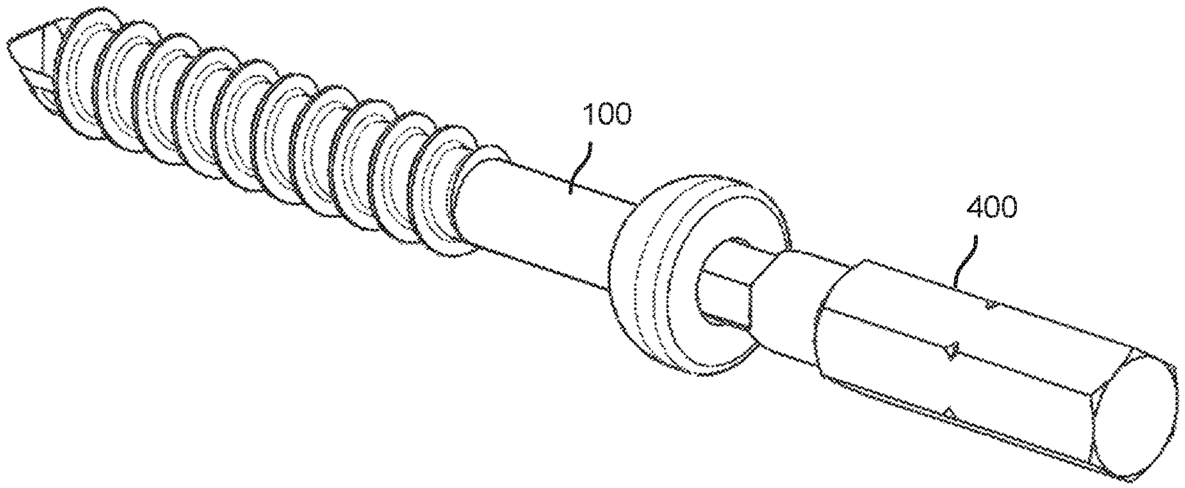
Figure 5C:
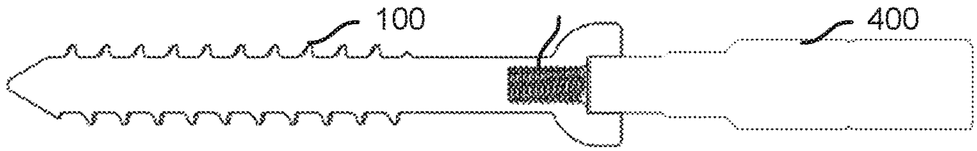

FIGS. 5A-5C are diagrams illustrating examples of engaging a head driver tool with a fastener. Head driver tool 400 of FIG. 4 is engaged with fastener 100 of FIGS. 1A-1F. Tip 402 of head driver tool 400 engages walls of drive recess 110 via press fit. Rotation of head driver tool 400 rotates fastener 100 to screw or unscrew fastener 100.

Figure 6A:
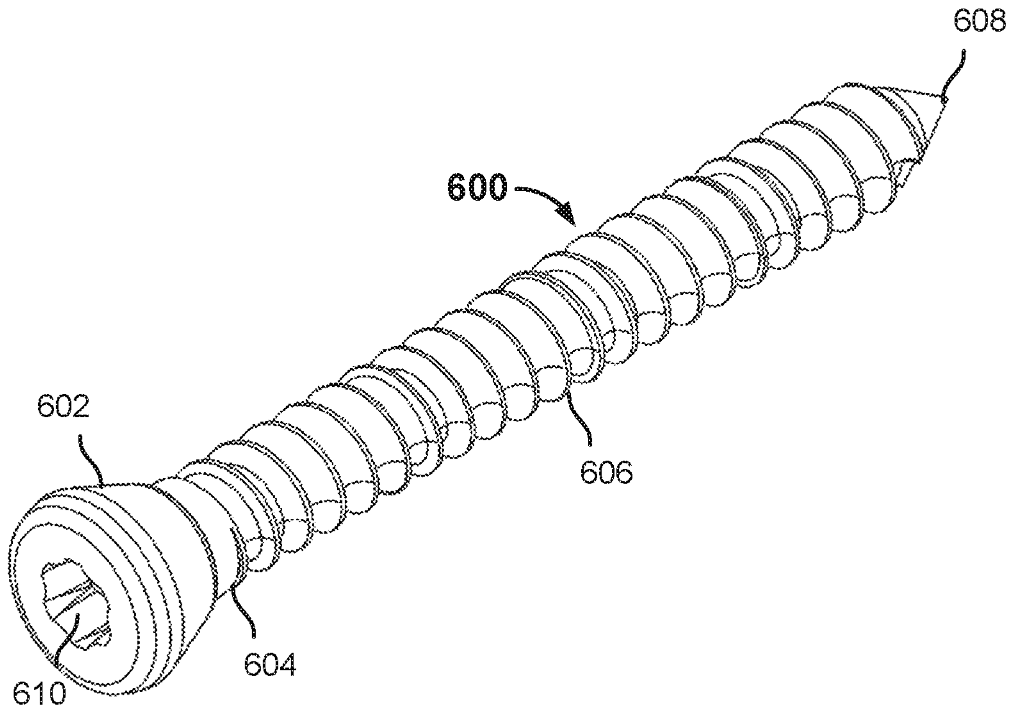
FIGS. 6A-6C are diagrams illustrating various views of alternate embodiments of the fastener shown in FIGS. 1A-1F.
Figure 6B:
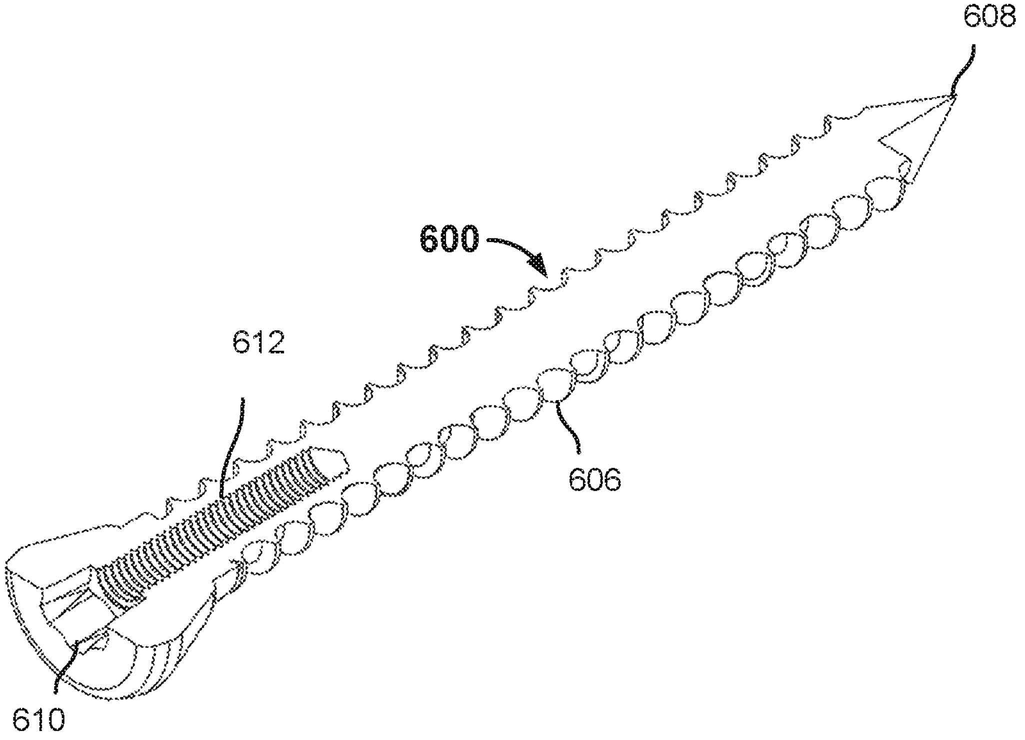
Figure 6C:
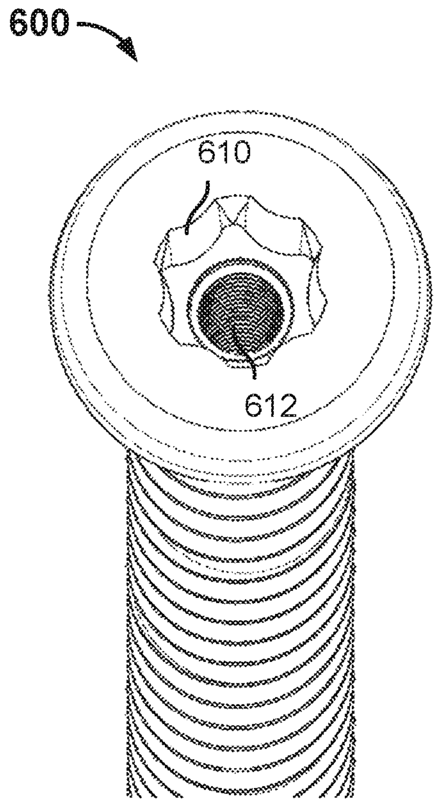

FIGS. 6A-6C are diagrams illustrating various views of alternate embodiments of the fastener shown in FIGS. 1A-1F. FIG. 6B is a diagram illustrating a section view of the embodiment of the fastener. Fastener 600 (e.g., screw) includes head 602, shank 604, threads 606, tip 608, drive recess 610, and internal threads 612. As compared to fastener 100, fastener 600 has a shorter shank portion, different thread type (i.e., cortical) and a different drive recess type (e.g., hexalobular, star/torx).

Figure 7:
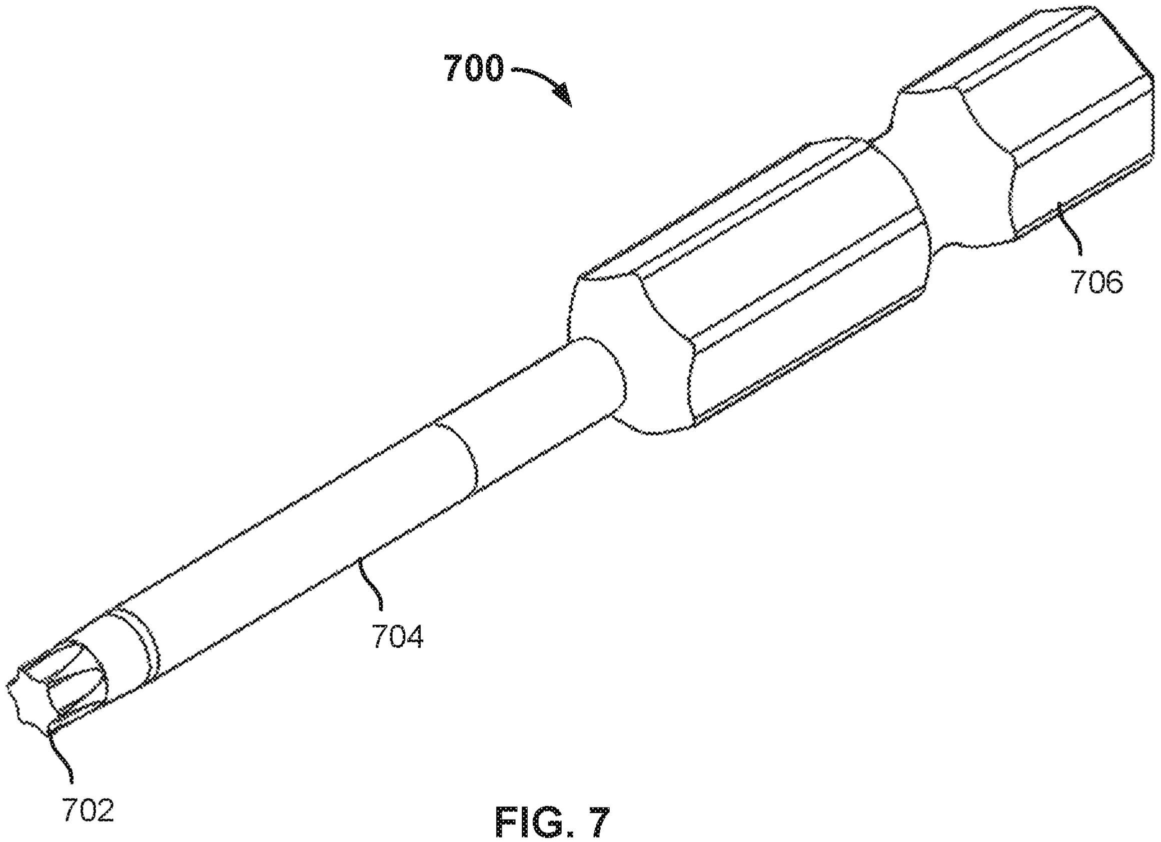
FIG. 7 is a diagram illustrating an embodiment of a head driver tool.

FIG. 7 is a diagram illustrating an embodiment of a head driver tool. Head driver tool 700 (e.g., driver bit) includes distal Hexalobular tip 702, elongated neck portion 704, and driver engagement shank 706. Tool 700 is an alternate embodiment of head driver tool 400 of FIG. 4. Hexalobular tip 702 is configured to cooperate with internal walls of drive recess 610 of fastener 600 shown in FIGS. 6A-6C. Shank 706 is configured to engage a chuck or a driver bit retainer of a driver power or hand tool.

Figure 8:
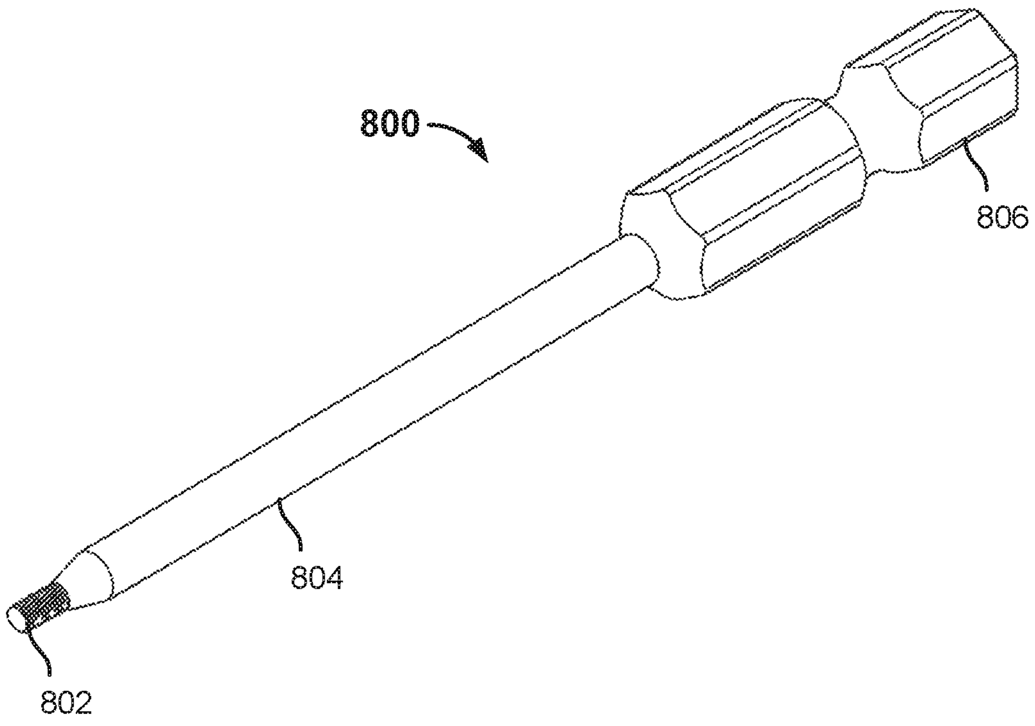
FIG. 8 is a diagram illustrating an embodiment of an interlock driver tool.

FIG. 8 is a diagram illustrating an embodiment of an interlock driver tool. Interlock driver tool 800 (e.g., driver bit) includes distal tip 802 with threads, elongated neck portion 804, and driver engagement shank 806. Threads of tip 802 are configured to cooperate with internal threads 112 of fastener 100 shown in FIGS. 1A-1F and/or internal threads 612 of fastener 600 shown in FIGS. 6A-6C. Tool 800 is an alternate embodiment of interlock driver tool 200 of FIG. 2.

Figure 9:
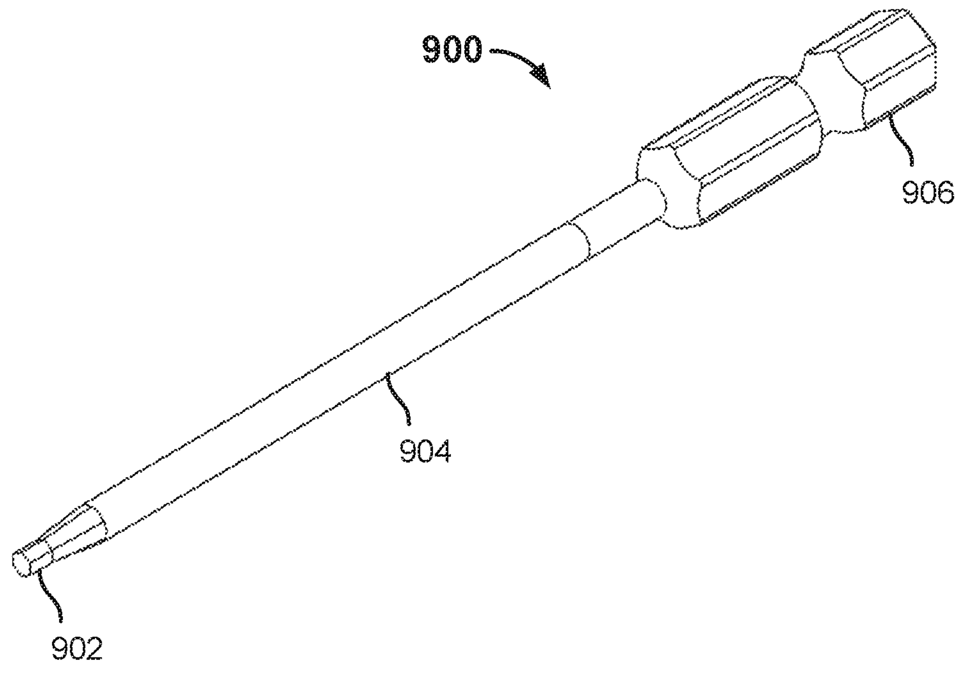
FIG. 9 is a diagram illustrating an embodiment of a head driver tool.

FIG. 9 is a diagram illustrating an embodiment of a head driver tool. Head driver tool 900 (e.g., driver bit) includes distal hex tip 902, elongated neck portion 904, and driver engagement shank 906. Tool 900 is an alternate embodiment of head driver tool 400 of FIG. 4 with elongated neck portion 904. Tip 902 is configured to cooperate with internal walls of drive recess 110 of fastener 100 shown in FIGS. 1A-1F. Shank 906 is configured to engage a chuck or a driver bit retainer of a driver power or hand tool.

Figure 10A:
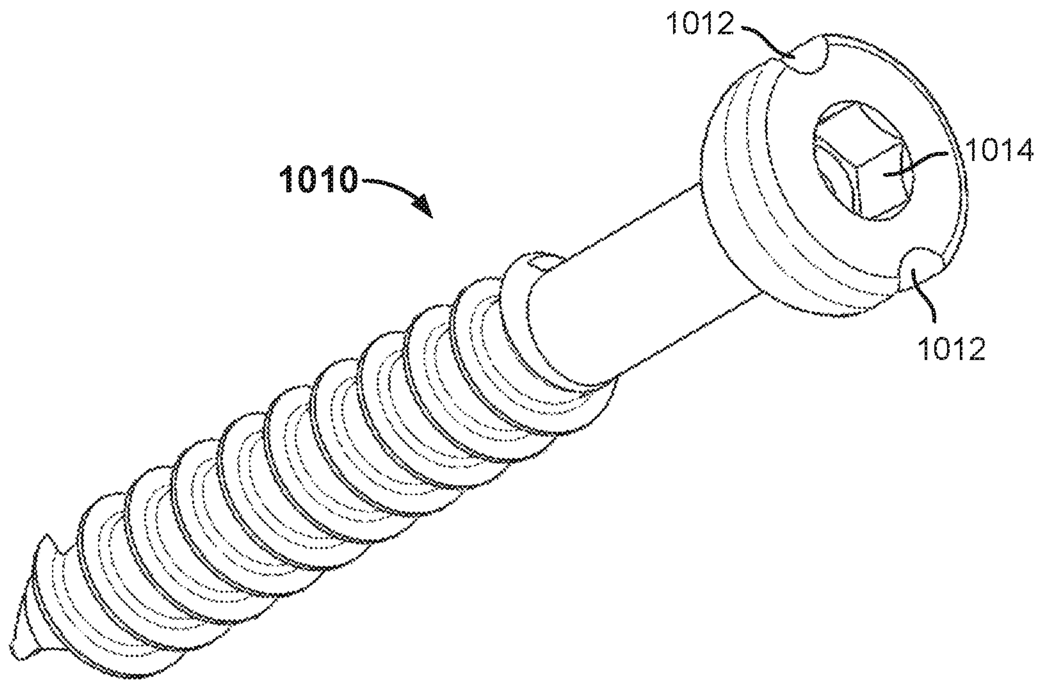
FIGS. 10A-10P are diagrams illustrating various views of different embodiments of fasteners with secondary drive features.
Figure 10B:
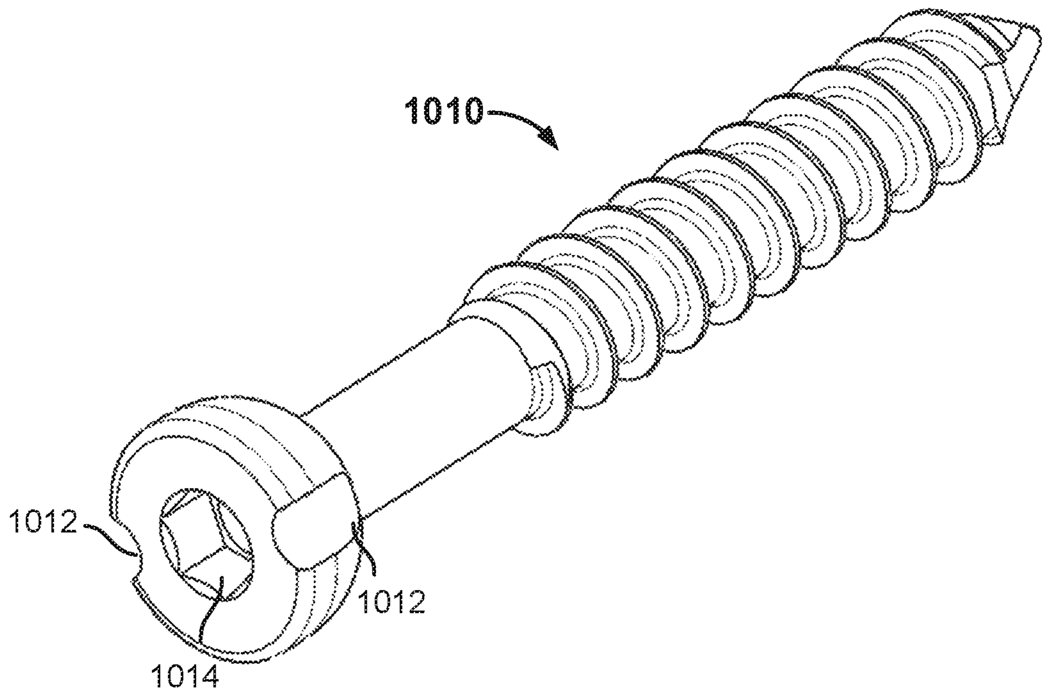
Figure 10C:
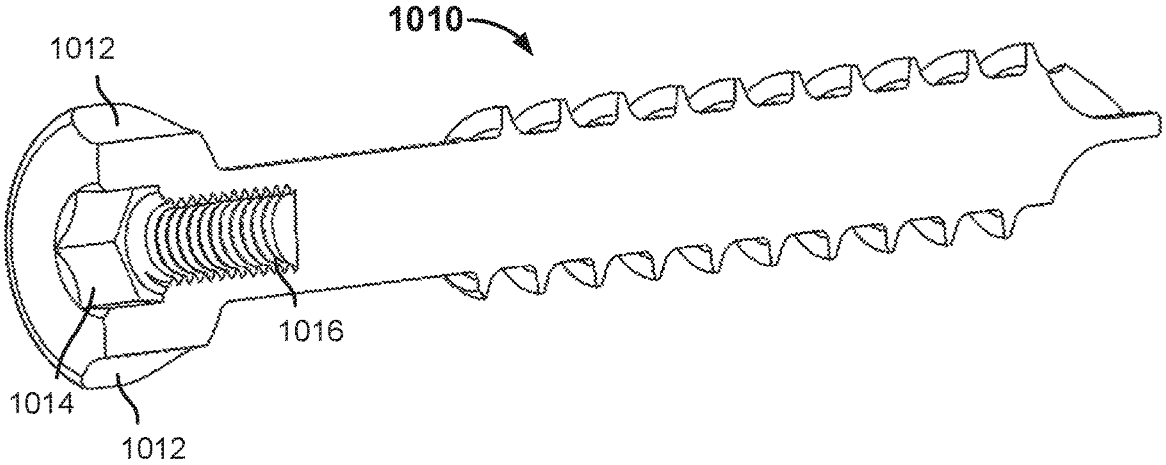
Figure 10D:
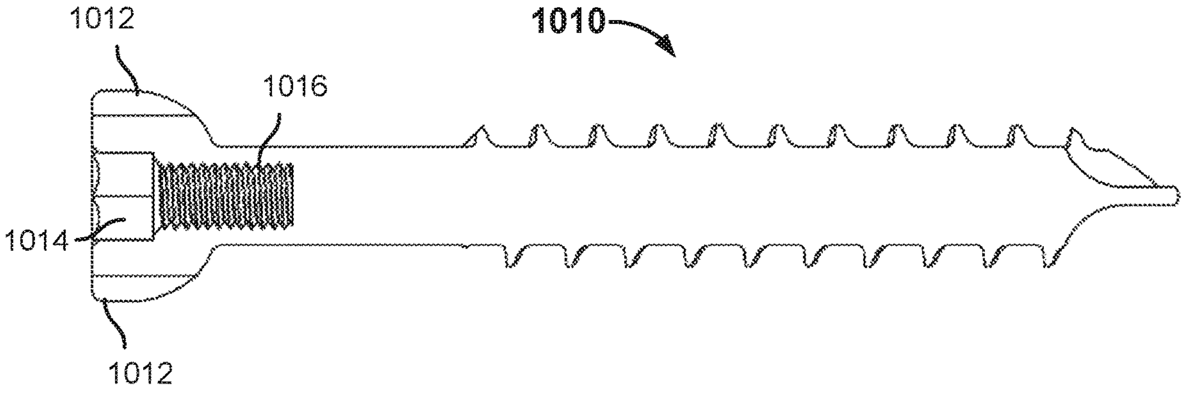
Figure 10E:
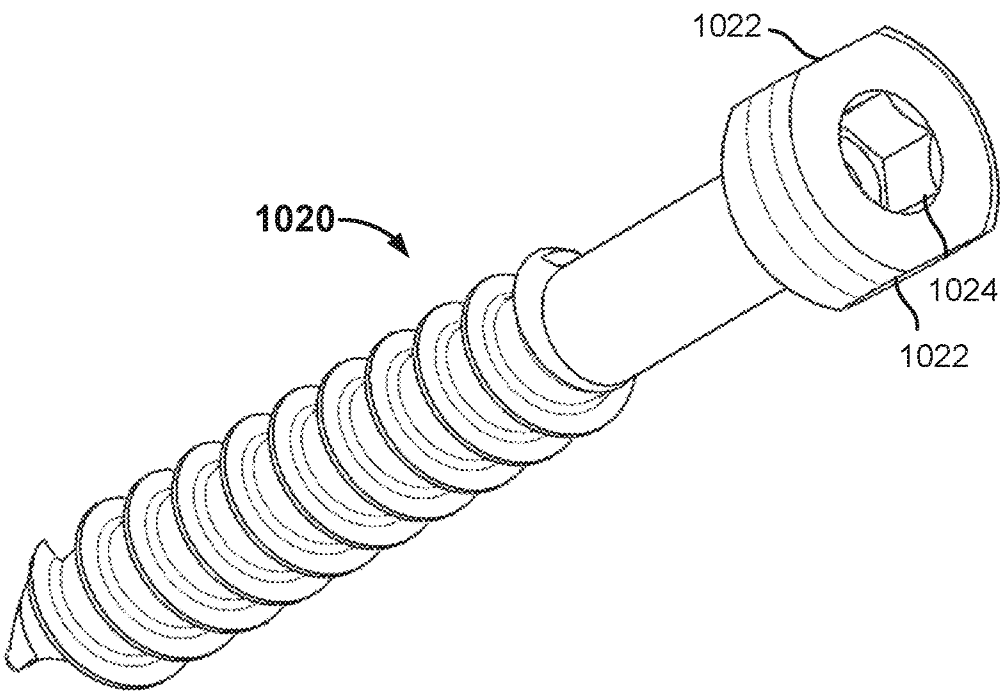
Figure 10F:
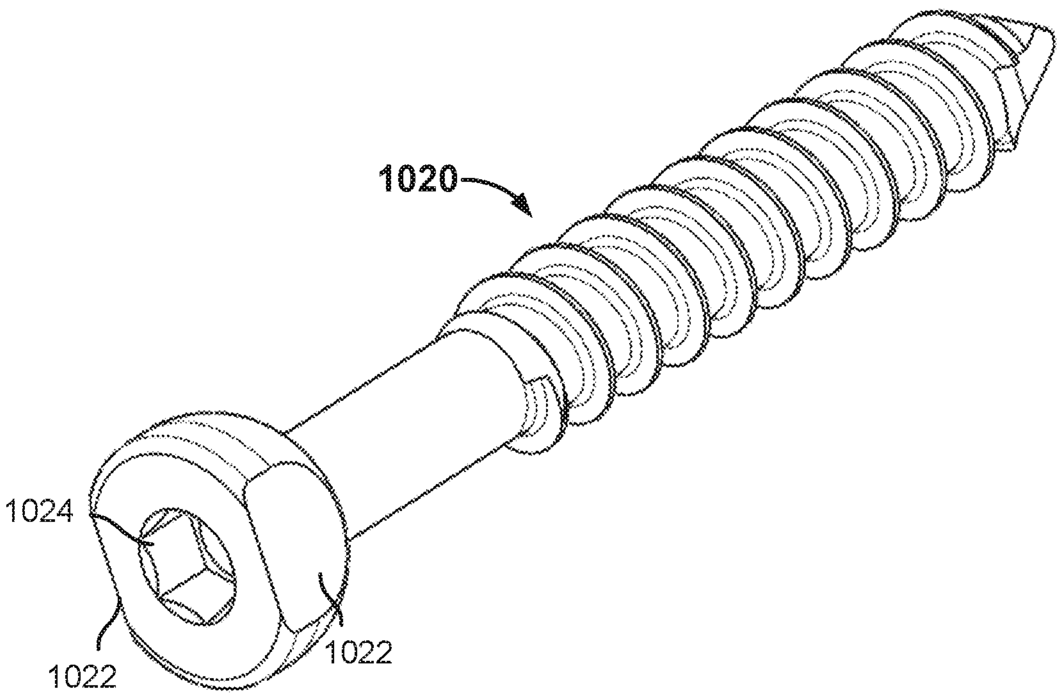
Figure 10G:
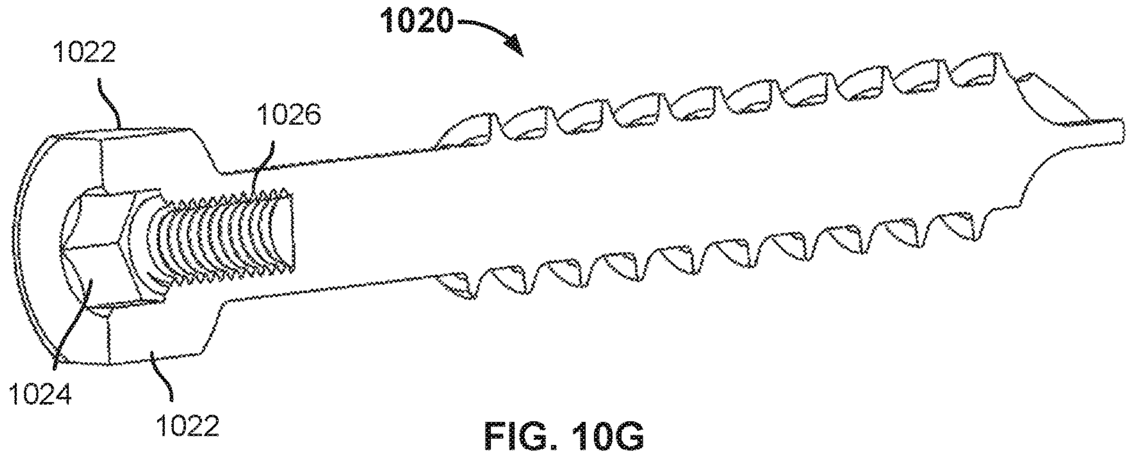
Figure 10H:
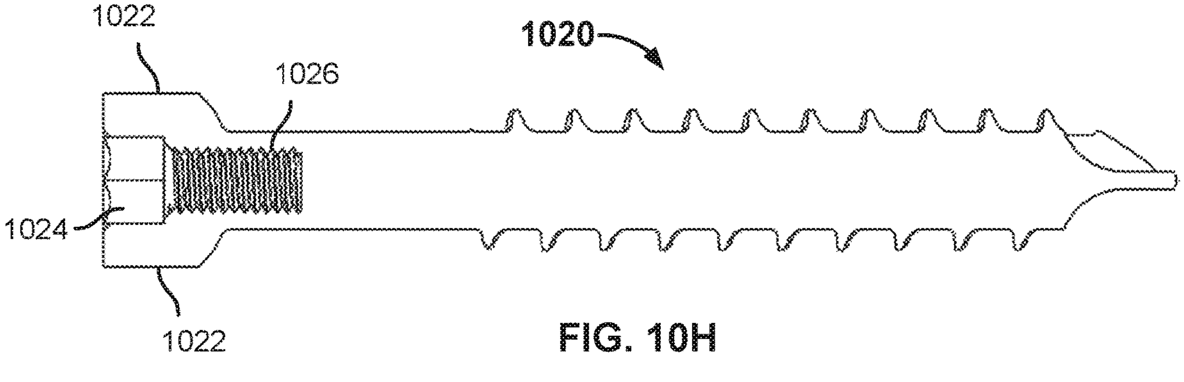
Figure 10I:
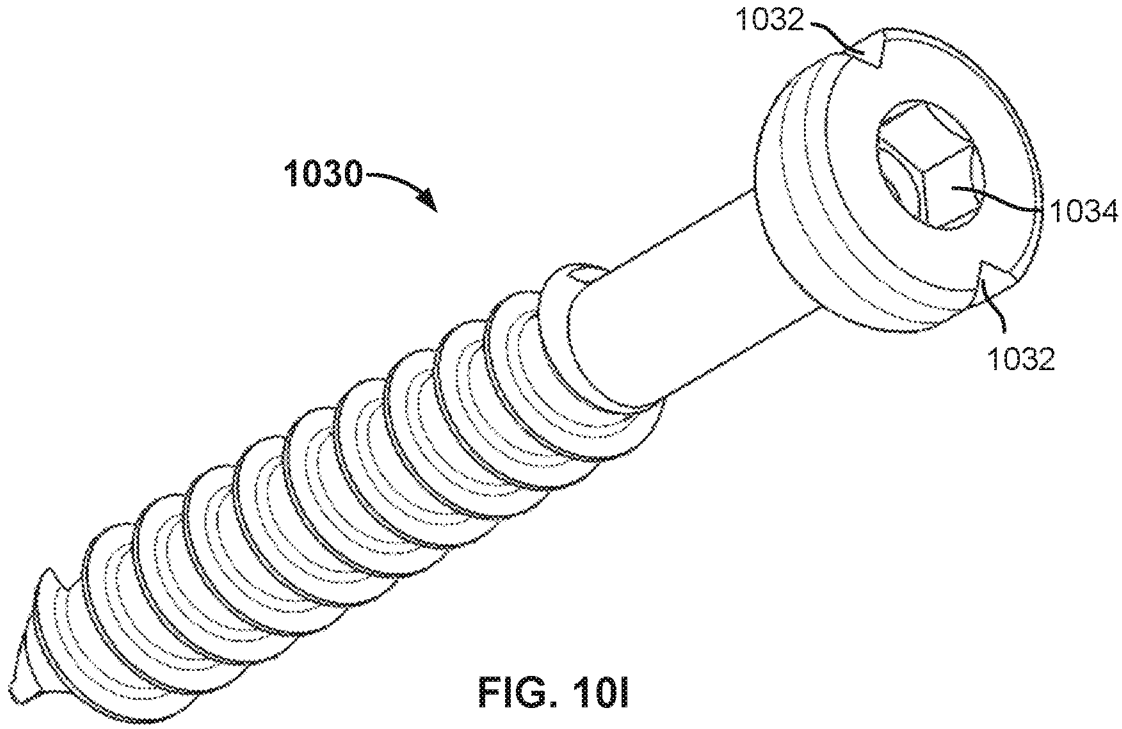
Figure 10J:
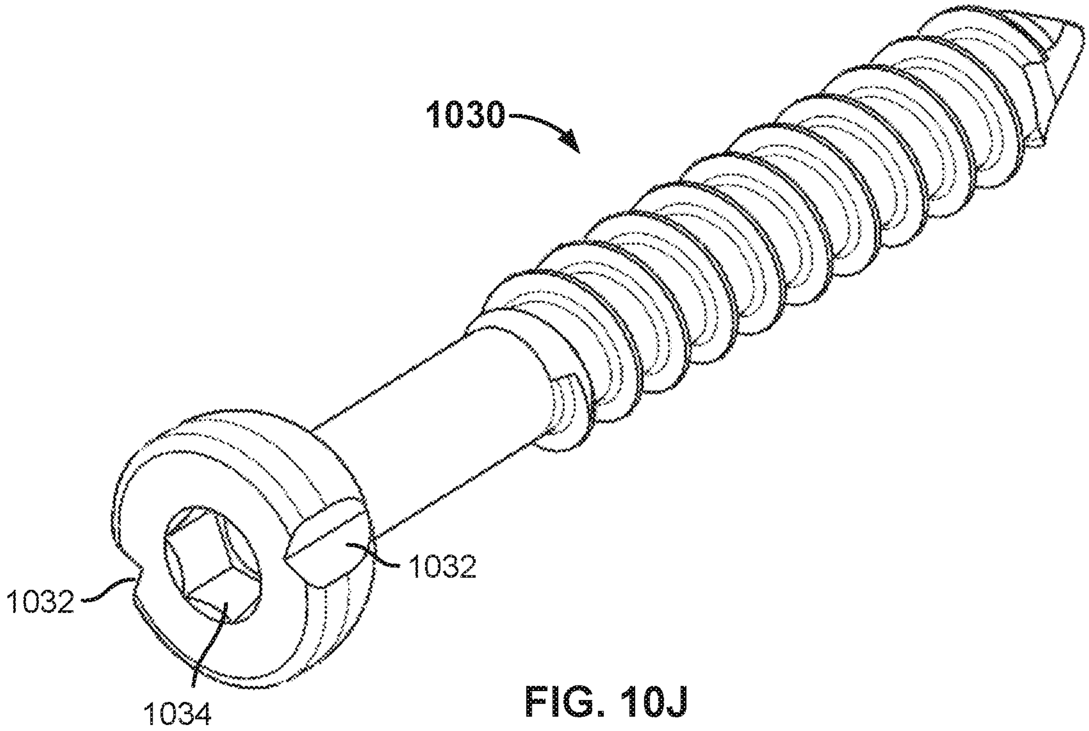
Figure 10K:
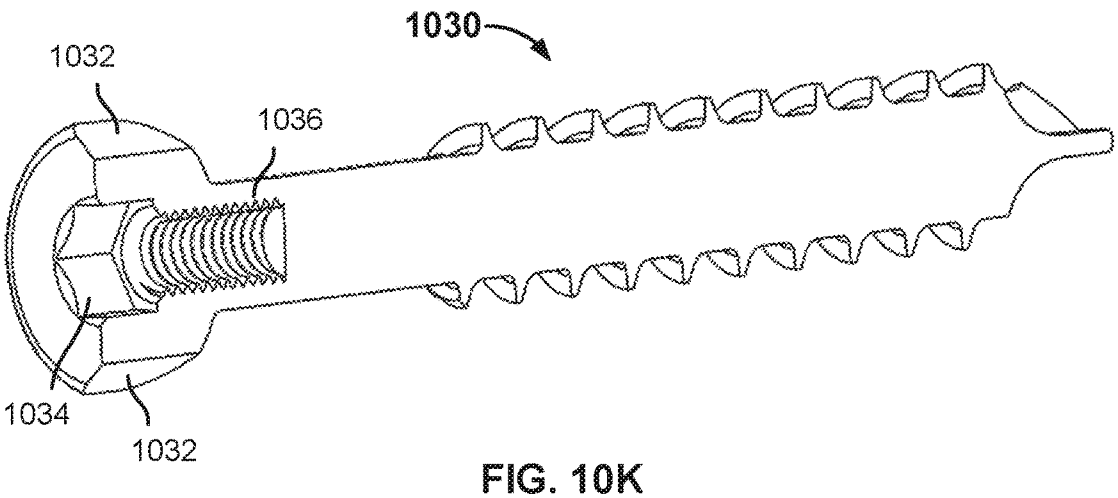
Figure 10L:
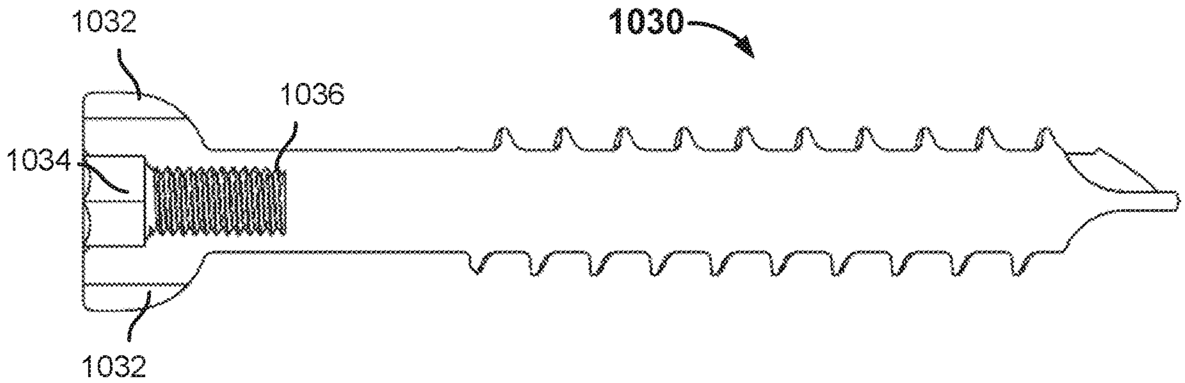
Figure 10M:
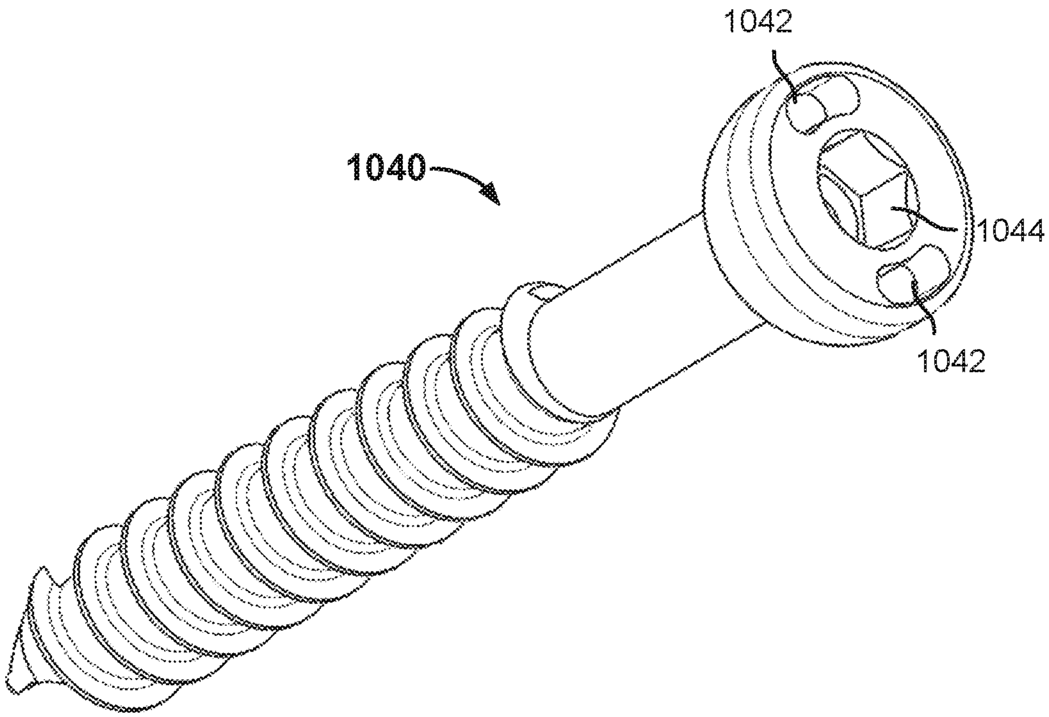
Figure 10N:
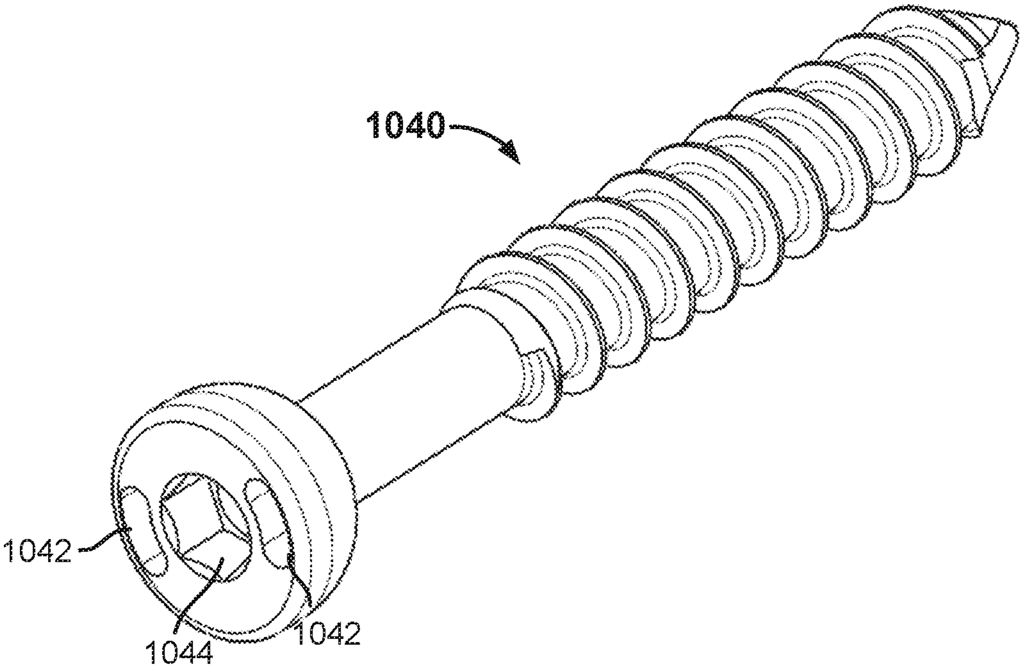
Figure 10O:
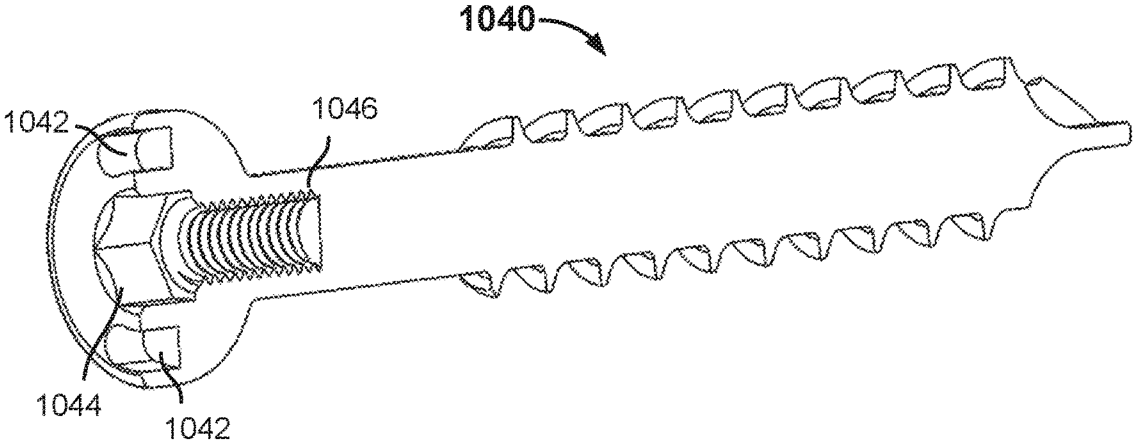
Figure 10P:
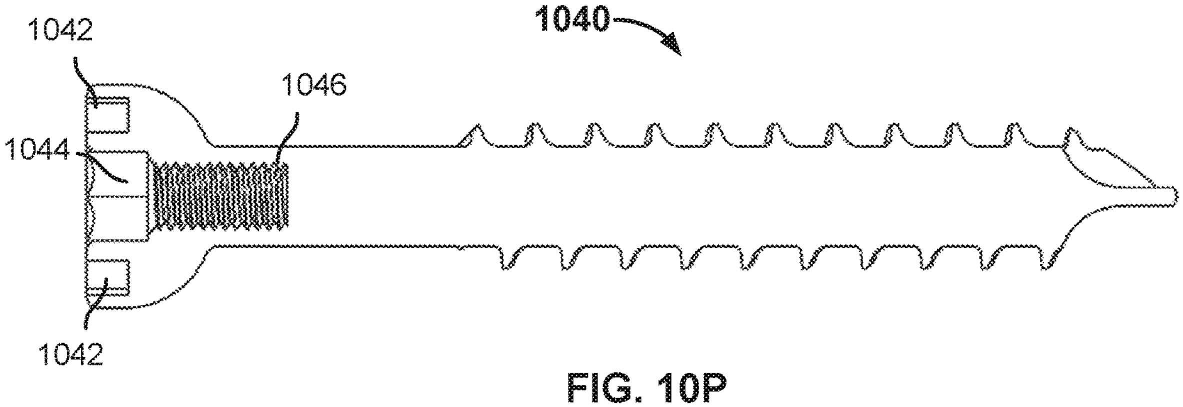

FIGS. 10A-10P are diagrams illustrating various views of different embodiments of fasteners with secondary drive features. The various different embodiments of shown external and recessed drive features are merely examples, and other shapes, locations, configurations, and instance numbers of drive features exist in other embodiments.

FIGS. 10A-10B are diagrams illustrating various views of an embodiment of fastener 1010 with half-moon external drive features. FIGS. 10C-10D are diagrams illustrating section views of the embodiment of fastener 1010. In some embodiments, fastener 1010 includes the features of fastener 100 shown in FIGS. 1A-1F. In addition to these features shared with fastener 100, fastener 1010 includes half-moon external drive features 1012 shaped on the sides of the fastener's proximal head. Although two instances of external drive features 1012 are shown, any number of these external drive features may exist in other embodiments. In some embodiments, half-moon external drive features 1012 are utilized to further secure the fastener to a tool (e.g., screwdriver, power tool, etc.) utilized to rotate/drive the fastener. For example, features 1012 function as external head drive features to engage corresponding surface(s) and/or protrusion(s) of a tool to secure fastener 1010 to the tool when fastener 1010 is being rotated via the tool. In some embodiments, external drive features 1012 are utilized in conjunction with center drive recess 1014 and/or internal threads 1016 when securing fastener 1010 to the tool utilized to rotate/drive the fastener. For example, the tool includes a first mechanism to engage center drive recess 1014 and/or internal threads 1016 in conjunction with a second mechanism to engage external drive features 1012.

FIGS. 10E-10F are diagrams illustrating various views of an embodiment of fastener 1020 with flat external drive features. FIGS. 10G-10H are diagrams illustrating section views of the embodiment of fastener 1020. In some embodiments, fastener 1020 includes the features of fastener 100 shown in FIGS. 1A-1F. In addition to these features shared with fastener 100, fastener 1020 includes flat external drive features 1022 shaped on the sides of the fastener's proximal head. Although two instances of external drive features 1022 are shown, any number of these external drive features may exist in other embodiments. In some embodiments, flat external drive features 1022 are utilized to further secure the fastener to a tool (e.g., screwdriver, power tool, etc.) utilized to rotate/drive the fastener. For example, features 1022 function as external head drive features to engage corresponding surface(s) and/or protrusion(s) of a tool to secure fastener 1020 to the tool when fastener 1020 is being rotated via the tool. In some embodiments, external drive features 1022 are utilized in conjunction with center drive recess 1024 and/or internal threads 1026 when securing fastener 1020 to the tool utilized to rotate/drive the fastener. For example, the tool includes a first mechanism to engage center drive recess 1024 and/or internal threads 1026 in conjunction with a second mechanism to engage external drive features 1022.

FIGS. 10I-10J are diagrams illustrating various views of an embodiment of fastener 1030 with triangular external drive features. FIGS. 10K-10L are diagrams illustrating section views of the embodiment of fastener 1030. In some embodiments, fastener 1030 includes the features of fastener 100 shown in FIGS. 1A-1F. In addition to these features shared with fastener 100, fastener 1030 includes triangular external drive features 1032 shaped on the sides of the fastener's proximal head. Although two instances of external drive features 1032 are shown, any number of these external drive features may exist in other embodiments. In some embodiments, triangular external drive features 1032 are utilized to further secure the fastener to a tool (e.g., screwdriver, power tool, etc.) utilized to rotate/drive the fastener. For example, features 1032 function as external head drive features to engage corresponding surface(s) and/or protrusion(s) of a tool to secure fastener 1030 to the tool when fastener 1030 is being rotated via the tool. In some embodiments, external drive features 1032 are utilized in conjunction with center drive recess 1034 and/or internal threads 1036 when securing fastener 1030 to the tool utilized to rotate/drive the fastener. For example, the tool includes a first mechanism to engage center drive recess 1034 and/or internal threads 1036 in conjunction with a second mechanism to engage external drive features 1032.

FIGS. 10M-10N are diagrams illustrating various views of an embodiment of fastener 1040 with recessed pin drive features. FIGS. 10O-10P are diagrams illustrating section views of the embodiment of fastener 1040. In some embodiments, fastener 1040 includes the features of fastener 100 shown in FIGS. 1A-1F. In addition to these features shared with fastener 100, fastener 1040 includes recessed arc-shaped pin drive features 1042 recessed on the top of the fastener's proximal head offset from center drive recess 1044. Although two instances of recessed arc-shaped pin drive features 1042 are shown, any number of these recessed drive features may exist in other embodiments. In some embodiments, recessed arc-shaped pin drive features 1042 are utilized to further secure the fastener to a tool (e.g., screwdriver, power tool, etc.) utilized to rotate/drive the fastener. For example, features 1042 function as additional recessed head drive features to engage corresponding pins(s) and/or protrusion(s) of a tool to secure fastener 1040 to the tool when fastener 1040 is being rotated via the tool. In some embodiments, recessed arced-shaped pin drive features 1042 are utilized in conjunction with center drive recess 1044 and/or internal threads 1046 when securing fastener 1040 to the tool utilized to rotate/drive the fastener. For example, the tool includes a first mechanism to engage center drive recess 1044 and/or internal threads 1046 in conjunction with a second mechanism to engage recessed arc-shaped pin drive features 1042.

Figure 11A:
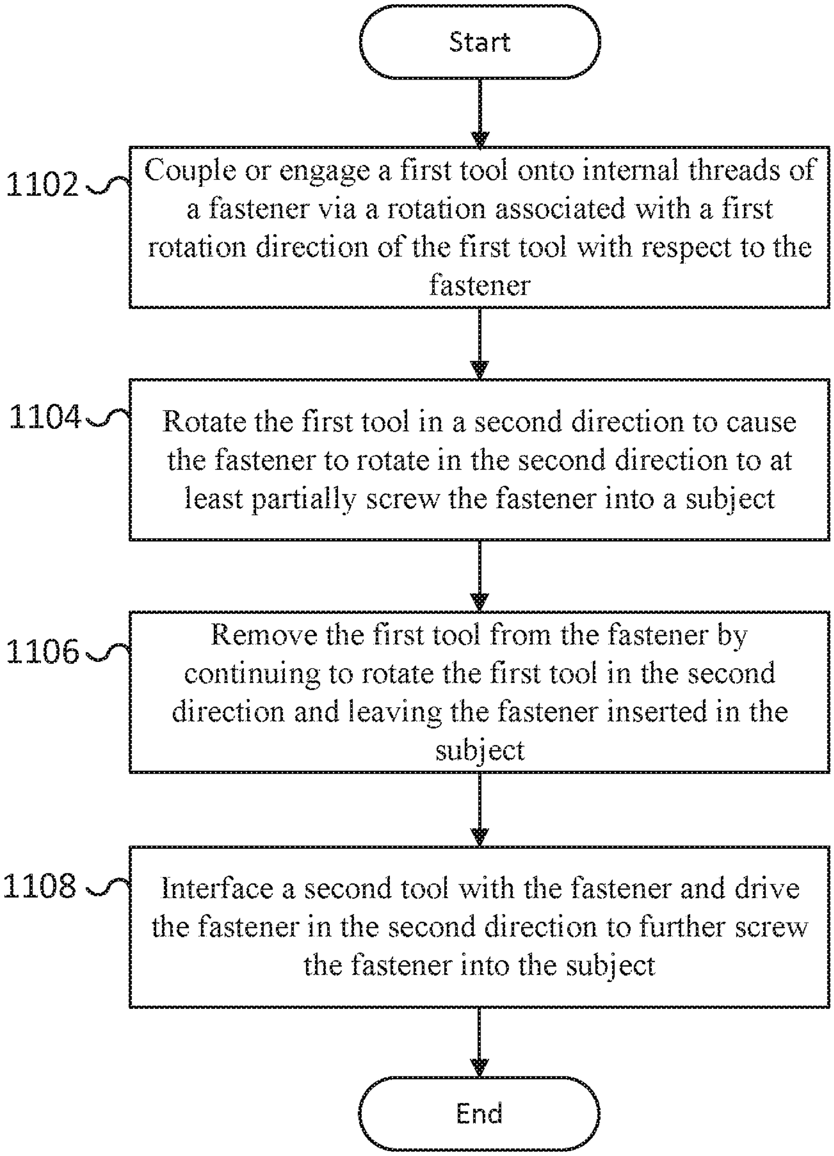
FIG. 11A is a flowchart illustrating an embodiment of a process for inserting a fastener into a subject.

FIG. 11A is a flowchart illustrating an embodiment of a process for inserting a fastener into a subject. FIG. 11B is a diagram illustrating an example implementation of at least a portion of the process of FIG. 11A. In some embodiments, at least a portion of the process of FIG. 11A is performed during a surgical operation associated with one or more of the following: lumbosacral, acetabulum, hip, pelvis, thoracic, or spinal. In some embodiments, the process of FIG. 11A is used to insert fastener 100 of FIGS. 1A-1F, fastener 600 of FIGS. 6A-6C, fastener 1010 of FIGS. 10A-10D, fastener 1020 of FIGS. 10E-10H, fastener 1030 of FIGS. 10I-10L, and/or fastener 1040 of FIGS. 10M-10P to a subject.

At 1102, a first tool is coupled or mated onto internal threads of a fastener. This coupling or mating may be achieved by rotating the first tool and/or the fastener such that with respect to the fastener, the first tool is rotated in a first direction to screw a tip of the first tool into the fastener. Examples of the first tool include interlock driver tool 200 shown in FIGS. 2A-2B or interlock driver tool 800 shown in FIG. 8. In some embodiments, the first tool (e.g., interlock driver bit) is coupled or mated to a surgical electronic/manual driver operated by a surgeon to rotate the first tool. An example of step 1102 is shown in setup step 1 of FIG. 11B where the interlock driver is inserted into the screw's left-handed internally threaded chamber by rotating it counterclockwise.

At 1104, the first tool is rotated in a second direction to cause the fastener to rotate in the second direction to at least partially screw the fastener into a subject. The second direction is opposite the first direction. At 1106, the first tool is removed from the fastener by continuing to rotate the first tool in the second direction and leaving the fastener at least partially inserted in the subject. An example of steps 1104 and 1106 are shown in insertion step 2 of FIG. 11B where the screw coupled or mated to the interlock driver tool is placed at a desired position on the subject, and the screw is inserted by rotating the screw via the interlock driver tool clockwise into the subject (e.g., bone). Once a few of the external threads of the screw have been seated into the subject, the opposing torques from the turning of the interlock driver tool and the resistance of being inserted in the subject unscrews the interlock driver tool from the internal threads of the screw.

At 1108, a second tool is interfaced with the fastener to drive the fastener in the second direction to further screw the fastener into the subject. Examples of the second tool include fastener head driver tool 400 shown in FIG. 4, fastener head driver tool 700 shown in FIG. 7, or fastener head driver tool 900 shown in FIG. 9. In some embodiments, the second tool is interfaced with the fastener via a drive recess or an external or recessed drive configuration of the fastener. In some embodiments, the second tool (e.g., fastener head driver bit) is coupled or mated to a surgical electronic/manual driver operated by a surgeon to rotate the second tool. An example of step 1108 is shown in insertion tighten step 3 of FIG. 11B where once the interlock driver tool is removed from the screw, a secondary driver is utilized to interface with the head of the screw and rotated in the clockwise direction to complete the insertion and fasten the screw to a desired tightness. In some embodiments, because biomaterial can accumulate inside the internally threaded cavity of the fastener, the cavity with the internal threads may be in part filled with hydrogel or another soluble and/or biocompatible material to reduce the accumulation of biomaterial inside the cavity.

Figure 12A:
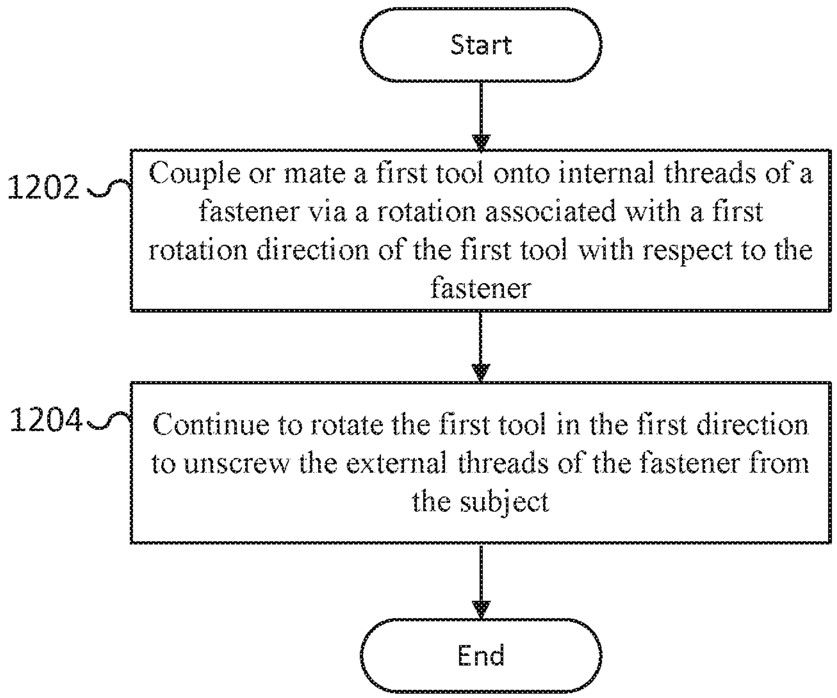
FIG. 12A is a flowchart illustrating an embodiment of a process for removing a fastener from a subject.
Figure 12B:
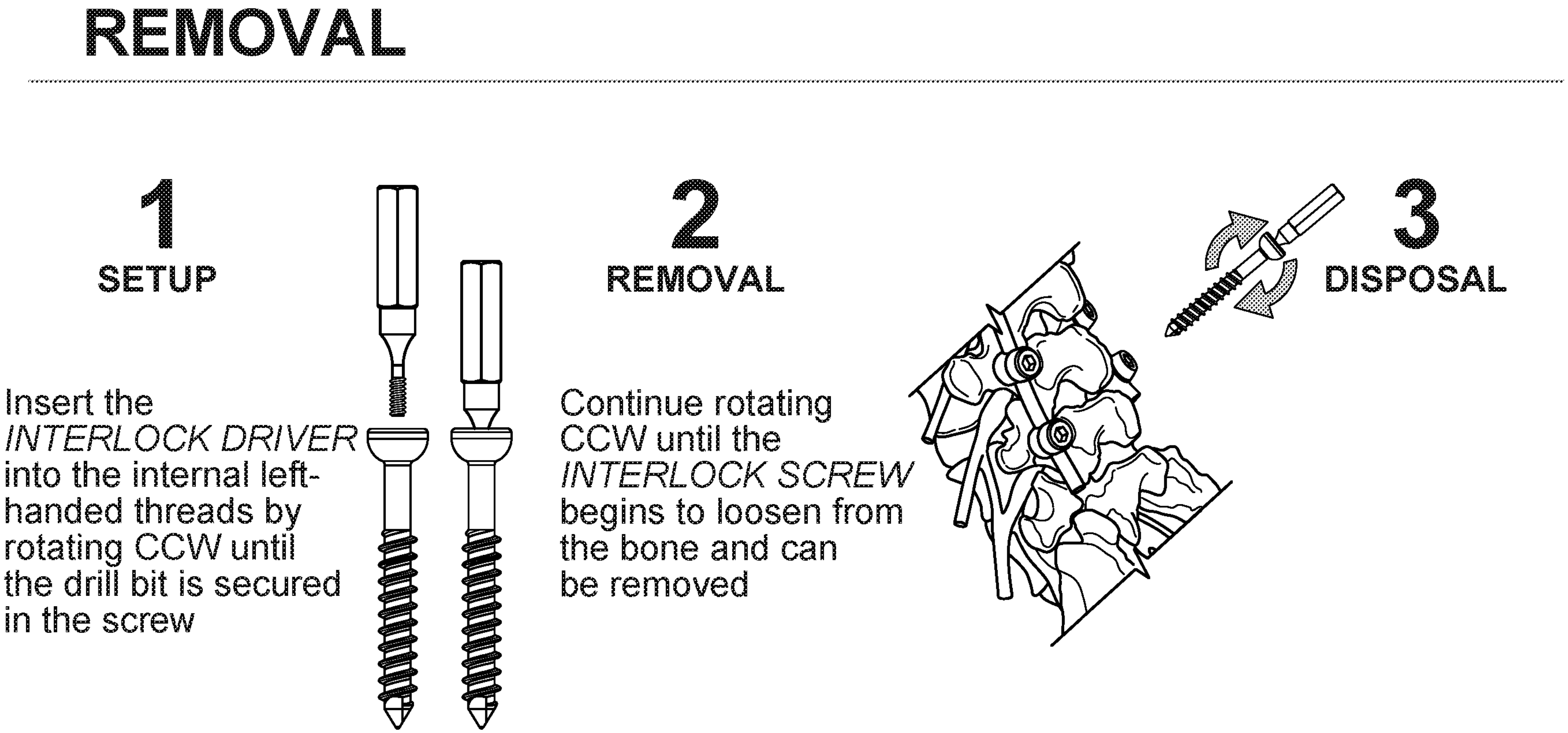
FIG. 12B is a diagram illustrating an example implementation of at least a portion of the process of FIG. 12A.

FIG. 12A is a flowchart illustrating an embodiment of a process for removing a fastener from a subject. FIG. 12B is a diagram illustrating an example implementation of at least a portion of the process of FIG. 12A. In some embodiments, at least a portion of the process of FIG. 12A is performed during a surgical operation associated with one or more of the following: lumbosacral, acetabulum, hip, pelvis, thoracic, or spinal. In some embodiments, the process of FIG. 12 is used to remove fastener 100 of FIGS. 1A-1F, fastener 600 of FIGS. 6A-6C, fastener 1010 of FIGS. 10A-10D, fastener 1020 of FIGS. 10E-10H, fastener 1030 of FIGS. 10I-10L, and/or fastener 1040 of FIGS. 10M-10P from a subject.

At 1202, a first tool is coupled or mated onto internal threads of a fastener inserted in a subject. This coupling or mating may be achieved by rotating the first tool such that with respect to the fastener, the first tool is rotated in a first direction to screw a tip of the first tool into the fastener. Internal threads of the fastener can be utilized for fastener removal in cases where a stripped, broken (e.g., a screw whose head is broken off), or otherwise damaged surgical screw needs to be removed from the body. The internal threads allow screws to be removed without having to drill into the patient's biological material that surrounds the screw and/or prevents the need to utilize extractor kits, or other extensive procedures. With respect to the fastener, the first tool is rotated in a first direction to screw a tip of the first tool into the fastener. Examples of the first tool include interlock driver tool 200 shown in FIGS. 2A-2B or interlock driver tool 800 shown in FIG. 8. In some embodiments, the first tool (e.g., interlock driver bit) is coupled or mated to a surgical electronic/manual driver operated by a surgeon to rotate the first tool. In some embodiments, prior to coupling or mating the first tool onto the internal threads of the fastener, accumulated biomaterial or prior placed filler material (e.g., hydrogel or another soluble and/or biocompatible material) is removed (e.g., using a pick tool) from a cavity having the internal threads of the fastener. An example of step 1202 is shown in setup step 1 of FIG. 12B where the interlock driver is inserted into the screw's left-handed internally threaded cavity by rotating it counterclockwise.

At 1204, the rotation of the first tool is continued in the first direction to unscrew the external threads of the fastener from the subject. Given the opposing handedness of the internal threads and the external threads of the fastener, the direction of rotation of the first tool to insert it into the fastener is the same rotational direction to unscrew the fastener from the subject. With continual rotation, the first tool becomes fully engaged and bottoms out inside the fastener cavity with the internal threads, and the rotation of the first tool causes the fastener to rotate and become unscrewed from the subject. An example of step 1204 is shown in removal step 2 of FIG. 12B where the continued rotation of the interlock driver in the counterclockwise direction causes the screw to become loosened until it is removed from the subject. Step 3 of FIG. 12B shows that after removal, the screw can be safely disposed. The use of the first tool and the internal threads of the fastener to remove the fastener is especially useful when a drive recess of the fastener is damaged, stripped, or worn, preventing full engagement of a second tool configured to engage the drive recess of the fastener.

Although the foregoing embodiments have been described in some detail for purposes of clarity of understanding, the invention is not limited to the details provided. There are many alternative ways of implementing the invention. The disclosed embodiments are illustrative and not restrictive.

What is claimed is:

1. A system, comprising:

a fastener device, comprising:

a proximal head;

a shaft extending from the proximal head and having external threads on at least a portion of the shaft; and a chamber extending internally from the proximal head into the shaft, the chamber having internal threads along a substantial entirety of a length of the chamber;

wherein the external threads have a first handedness, and the internal threads have a second handedness different from the first handedness;

wherein features of the first handedness of the external threads and the second handedness of the internal threads are governed by a relative torque relationship; and wherein the relative torque relationship is determined based on one or more thread geometry parameters of one or both of the external threads and the internal threads; and a tool including a tip, wherein the tool is configured to:

rotate with respect to the fastener device in one direction to couple or mate the tip onto the internal threads of the fastener device, wherein the one direction relates to a clockwise direction or a counterclockwise direction, and wherein the fastener device is screwed in a subject; and continue to rotate in the one direction to unscrew the external threads of the fastener device from the subject.

2. The system of claim 1, wherein the first handedness is right-handed and the second handedness is left-handed.

3. The system of claim 1, wherein the tool includes an interlock drive tool including distal external threads, and wherein the fastener device is configured to be coupled or mated to the distal external threads cooperating with the internal threads of the chamber.

4. The system of claim 3, wherein the fastener device and the interlock driver tool are configured to unscrew from each other while the fastener device is being screwed at least partially into a subject.

5. The system of claim 3, wherein the fastener device and the interlock driver tool are configured to be seated together via the internal threads while the fastener device is being rotated for removal from a subject.

6. The system of claim 1, wherein the system further includes another tool, and wherein the fastener device is configured to be coupled or mated to a tool the other tool cooperating with the proximal head.

7. The system of claim 6, wherein the proximal head includes a drive recess and the other tool cooperates with the proximal head via the drive recess.

8. The system of claim 1, wherein the proximal head includes a drive recess that is one or more of the following shapes/types: slotted, cruciform, square, pentalobular, hexalobular, triangular, or tamper-resistant.

9. The system of claim 1, wherein the fastener device is made of non-ferrous material.

10. The system of claim 1, wherein the fastener device includes a self-tapping tip or a self-drilling tip.

11. The system of claim 1, wherein the external threads are of a cortical or cancellous thread type.

12. The system of claim 1, wherein the fastener device is a part of a pedicle screw.

13. The system of claim 1, wherein the fastener device is a cannulated screw with a hollow core.

14. The system of claim 1, wherein the chamber is at least partly filled or covered with a hydrogel or soluble material.

15. The system of claim 1, wherein the proximal head includes an external drive feature or a plurality of recessed drive features.

16. The system of claim 1, wherein the one or more thread geometry parameters include thread pitch, and/or thread profile dimensions.

17. The system of claim 1, wherein the one or more thread geometry parameters include a plurality of thread geometry parameters, and wherein the plurality of thread geometry parameters includes thread pitch and thread profile dimensions.

18. A system, comprising:

a fastener device, comprising:

a proximal head;

a shaft extending from the proximal head and having external threads on at least a portion of the shaft; and a chamber extending internally from the proximal head into the shaft, the chamber having internal threads along a substantial entirety of a length of the chamber;

wherein the external threads have a first handedness, and the internal threads have a second handedness different from the first handedness;

wherein features of the first handedness of the external threads and the second handedness of the internal threads are governed by a relative torque relationship; and wherein the relative torque relationship is determined based on one or more thread geometry parameters of one or both of the external threads and the internal threads;

a first tool, configure to:

rotate with respect to the fastener device in one direction to couple or mate to the fastener device, wherein the one direction relates to a clockwise direction or a counterclockwise direction;

rotate in another direction to cause the fastener device to rotate in the other direction to at least partially screw the fastener device into a subject; and continue to rotate in the other direction to be removed from the fastener device and leave the fastener device at least partially inserted in the subject; and a second tool, configure to:

interface with the proximal head of the fastener device; and rotate in the one direction to further insert the fastener device in the subject.

* * * * *